United States Patent
Wang et al.

(10) Patent No.: US 8,349,848 B2
(45) Date of Patent: Jan. 8, 2013

(54) PYRROLO[3,2-D]PYRIMIDINES THAT ARE SELECTIVE ANTAGONISTS OF $A_{2B}$ ADENOSINE RECEPTORS

(75) Inventors: Guoquan Wang, Charlottesville, VA (US); Robert D. Thompson, Charlottesville, VA (US)

(73) Assignee: Dogwoof Pharmaceuticals, Inc., Charlottesville, VA (US)

( * ) Notice: Subject to any disclaimer, the term of this patent is extended or adjusted under 35 U.S.C. 154(b) by 719 days.

(21) Appl. No.: 12/266,259

(22) Filed: Nov. 6, 2008

(65) Prior Publication Data
US 2009/0082347 A1    Mar. 26, 2009

Related U.S. Application Data

(62) Division of application No. 11/897,678, filed on Aug. 31, 2007, now Pat. No. 7,470,697.

(60) Provisional application No. 60/824,316, filed on Sep. 1, 2006.

(51) Int. Cl.
| | |
|---|---|
| *A61K 31/519* | (2006.01) |
| *A61P 11/06* | (2006.01) |
| *A61P 11/08* | (2006.01) |
| *A61P 37/08* | (2006.01) |
| *C07D 487/04* | (2006.01) |

(52) U.S. Cl. .................... 514/265.1; 544/280

(58) Field of Classification Search .............. 544/244, 544/280; 514/81, 265.1
See application file for complete search history.

(56) References Cited

OTHER PUBLICATIONS

U.S. Committee for Refugees and Immigrants pamphlet, downloaded Mar. 12, 2012, <http://www.uscrirefugees.org/2010Website/5_Resources/5_1_For_Refugees_Immigrants/5_1_1_Health/5_1_1_1_Healthy_Living_Toolkit/5_1_1_1_15_English/English_Asthma.pdf>.*
Zablocki et. al. (Expert Opinion, 2006, 16(10), pp. 1347-1357).*
Ramsdell, J.W., Chest, 2003, 123(4), pp. 971-973.*

* cited by examiner

*Primary Examiner* — Susanna Moore

(57) ABSTRACT

The present invention provides compounds of the following formula and pharmaceutical compositions that are selective antagonists of $A_{2B}$ adenosine receptors (ARs).

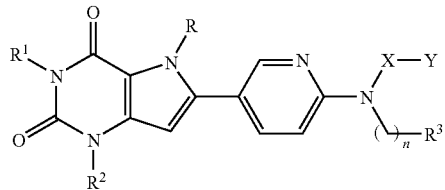

These compounds and compositions are useful as pharmaceutical agents.

18 Claims, No Drawings

PYRROLO[3,2-D]PYRIMIDINES THAT ARE SELECTIVE ANTAGONISTS OF $A_{2B}$ ADENOSINE RECEPTORS

This Application is a divisional application of U.S. application Ser. No. 11/897,678, filed Aug. 31, 2007, now U.S. Pat. No. 7,470,697, which claims the benefit of Provisional Application No. 60/824,316, filed Sep. 1, 2006, the disclosures of which are incorporated herein in their entirety.

FIELD OF THE INVENTION

The present invention relates to pyrrolo[3,2-d]pyrimidin-6-yl compounds and pharmaceutical compositions that are selective antagonists of the $A_{2B}$ adenosine receptor (AR). These compounds are useful as pharmaceutical agents.

BACKGROUND OF THE INVENTION

The alkylxanthine theophylline (below), a weak non-selective adenosine

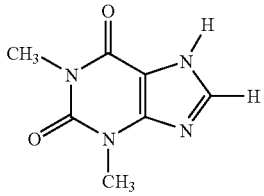

antagonist (See Linden, J., et al., *Cardiovascular Biology of Purines*, eds. G. Burnstock, et al., 1998, pp 1-20), is useful therapeutically for the treatment of asthma. However, its use is associated with unpleasant side effects, such as insomnia and diuresis. In recent years, the use of theophylline as a bronchodilator, for relief of asthma, has been supplanted by drugs of other classes, e.g., selective $\beta_2$-adrenergic agonists, corticosteroids, and recently leukotriene antagonists. These compounds also have limitations. Thus, the development of a theophylline-like drug with reduced side effects is still desirable.

It has been recognized that theophylline and its closely related analogue caffeine block endogenous adenosine acting as a local modulator of adenosine receptors in the brain and other organs at therapeutically useful doses. Adenosine activates four subtypes of G protein-coupled adenosine receptors (ARs), $A_1/A_{2A}/A_{2B}/A_3$. Enprofylline (below) is another example of a xanthine that has been reported to block $A_{2B}$ adenosine receptors and is used

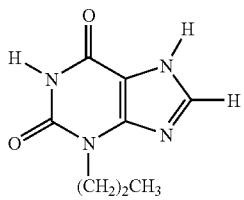

to treat asthma. However, this compound only weakly blocks $A_1$, $A_{2A}$, and $A_3$ adenosine receptors. It has also been shown by LaNoue et al (U.S. Pat. No. 6,060,481) that selective adenosine $A_{2B}$ antagonists are useful for improving insulin sensitivity in a patient.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381-402; and Robeva, A. S., et al., *Drug Dev. Res.* 1996, 39, 243-252). Enprofylline has a reported $K_i$ value of 7 μM and is somewhat selective in binding to human $A_{2B}$ ARs. (See Robeva, A. S., et al., *Drug Dev. Res.* 1996, 39, 243-252 and Linden, J., et al., *Mol. Pharmacol.* 1999, 56, 705-713). $A_{2B}$ ARs are expressed in some mast cells, such as the BR line of canine mastocytoma cells, which appear to be responsible for triggering acute $Ca^{2+}$ mobilization and degranulation. (See Auchampach, J. A., et al., *Mol. Pharmacol.* 1997, 52, 846-860 and Forsyth, P., et al., *Inflamm. Res.* 1999, 48, 301-307). $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13-18) endothelial-dependent vasodilation (See Martin, P. L., et al., *J. Pharmacol. Exp. Ther.* 1993, 265, 248-253), and fluid secretion from intestinal epithelia. (See Strohmeier, G. R., et al., *J Biol. Chem.* 1995, 270, 2387-2394). Adenosine acting through $A_{2B}$ ARs has also been reported to stimulate chloride permeability in cells expressing the cystic fibrosis transport regulator. (See Clancy, J. P., et al., *Am. J. Physiol.* 1999, 276, C361-C369.)

Recently Linden et al., (U.S. Pat. No. 6,545,002) have described a new group of compounds and pharmaceutical compositions that are selective antagonists of $A_{2B}$ adenosine receptors (ARs).

Although adenosine receptor subtype-selective probes are available for the $A_1$, $A_{2A}$, and $A_3$ ARs, only few selective antagonists are known for the $A_{2B}$ receptor. Therefore, a continuing need exists for compounds that are selective $A_{2B}$ receptor antagonists.

SUMMARY OF THE INVENTION

The present invention provides compounds that act as antagonists of $A_{2B}$ adenosine receptors and stereoisomers and pharmaceutically acceptable salts thereof.

The invention also provides pharmaceutical compositions comprising a compound of the present invention or stereoisomer or a pharmaceutically acceptable salt thereof in combination with a pharmaceutically acceptable excipient.

Additionally, the invention provides a therapeutic method for treating a pathological condition or symptom in a mammal, such as a human, wherein the activity, e.g., over-activity, of adenosine $A_{2B}$ receptors is implicated in one or more symptoms of the pathology and antagonism (i.e., blocking) is desired to ameliorate such symptoms. Thus, the present invention provides a method of treating a disease comprising administering a therapeutically effective amount of at least one compound of the present invention or a stereoisomer or pharmaceutically acceptable salt thereof, wherein the disease is selected from asthma, allergies, allergic diseases (e.g., allergic rhinitis and sinusitis), autoimmune diseases (e.g., lupus), pulmonary fibrosis, diarrheal diseases, insulin resistance, diabetes, obesity, prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy.

The invention provides a compound of the present invention for use in medical therapy.

The invention also provides the use of a compound of the present invention for the manufacture of a medicament.

The invention also includes a method comprising contacting a compound of the present invention, optionally having a radioactive isotope (radionuclide), such as, for example, tritium, radioactive iodine (e.g., $^{125}$I for binding assays or $^{123}$I for Spectral Imaging) and the like, with target $A_{2B}$ adenosine receptor sites comprising said receptors, in vivo or in vitro, so as to bind to said receptors. Cell membranes comprising bound $A_{2B}$ adenosine receptor sites can be used to measure the selectivity of test compounds for adenosine receptor subtypes or can be used as a tool to identify potential therapeutic agents for the treatment of diseases or conditions associated with $A_{2B}$-receptor mediation, by contacting said agents with said radioligands and receptors, and measuring the extent of displacement of the radioligand and/or binding of the agent.

DETAILED DESCRIPTION OF THE INVENTION

Applicants have discovered that compounds of the present invention can be useful for the treatment of diseases associated with deleterious $A_{2B}$ receptor activation or activity.

In an embodiment, the present invention provides novel compounds of formula I or a stereoisomer or a pharmaceutically acceptable salt thereof:

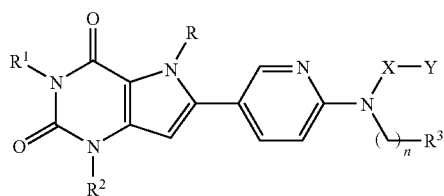

I wherein:

R is selected from: H, OH, $C_{1-6}$ alkyl, halo-$C_{1-8}$ alkyl, $C_{3-6}$ alkenyl, $C_{3-6}$ alkynyl, ($C_{3-8}$ cycloalkyl)$C_{1-8}$ alkylene, ($C_{4-10}$ heterocycle)$C_{1-8}$ alkylene, ($C_{6-10}$ aryl)$C_{1-8}$ alkylene, and ($C_{5-10}$ heteroaryl)$C_{1-8}$ alkylene, wherein R optionally is substituted by one $R^c$;

$R^c$ is independently selected from: F, Cl, Br, I, $C_{1-6}$ alkyl, $C_{2-6}$ alkenyl, $C_{2-6}$ alkynyl, $OC_{1-6}$ alkyl, $NO_2$, —CN, $CF_3$, and $OCF_3$;

$R^1$ and $R^2$ are independently selected from: H, $C_{1-8}$ alkyl, $C_{3-8}$ alkenyl, $C_{3-8}$ alkynyl, $C_{1-8}$ alkoxy, $C_{3-8}$ cycloalkyl, ($C_{3-8}$ cycloalkyl)$C_{1-8}$ alkylene, $C_{4-10}$ heterocycle, ($C_{4-10}$ heterocycle)$C_{1-8}$ alkylene, $C_{6-10}$ aryl, ($C_{6-10}$ aryl)$C_{1-8}$ alkylene, $C_{5-10}$ heteroaryl, and ($C_{5-10}$ heteroaryl)$C_{1-8}$ alkylene, wherein $R^1$ and $R^2$ are independently optionally substituted with 1-2 $R^{1a}$;

$R^{1a}$ is independently selected from: F, Cl, Br, I, $C_{1-6}$ alkyl, $C_{2-6}$ alkenyl, $C_{2-6}$ alkynyl, —$(CH_2)_aOR^a$, $(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_a$ $OC(O)R^a$, —$(CH_2)_aCONR^aR^a$, $CF_3$, and $OCF_3$;

$R^a$ is independently selected from: H, $C_{1-6}$ alkyl, $C_{2-6}$ alkenyl, $C_{2-6}$ alkynyl, $C_{3-8}$ cycloalkyl, ($C_{3-8}$ cycloalkyl)$C_{1-8}$ alkylene, $C_{4-10}$ heterocycle, ($C_{4-10}$ heterocycle)$C_{1-8}$ alkylene, $C_{6-10}$ aryl, ($C_{6-10}$ aryl)$C_{1-8}$ alkylene, $C_{5-10}$ heteroaryl, and ($C_{5-10}$ heteroaryl)$C_{1-8}$ alkylene, wherein the alkyl is optionally interrupted with 1-2 heteroatoms selected from the group consisting of —O—, —S(O)$_p$— and —NR$^b$—;

$R^b$ is independently selected from the group consisting of H, $C_{1-6}$ alkyl, and benzyl;

$R^3$ is selected from: OH, $C_{1-8}$ alkoxy, $NR^{3a}R^{3b}$, $C_{3-8}$ cycloalkyl, $C_{4-10}$ heterocycle, $C_{6-10}$ aryl, and $C_{5-10}$ heteroaryl, wherein the cycloalkyl, heterocycle, aryl, and heteroaryl optionally are substituted with 1-2 $R^{3c}$;

$R^{3a}$ and $R^{3b}$ are independently selected from: $C_{1-8}$ alkyl, $C_{2-8}$ alkenyl, $C_{2-8}$ alkynyl, phenyl, and benzyl;

$R^{3c}$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_a$ $OC(O)R^a$, —$(CH_2)_aCONR^aR^a$, $CF_3$, and $OCF_3$;

X is selected from: $(CH_2)_q$, $(CH_2)_rC(O)$, and $(CH_2)_rC(O)NR^4$;

$R^4$ is selected from: H, $C_{1-4}$ alkyl, $C_{1-4}$ alkoxy, and $C_{1-4}$ haloalkyl;

Y is selected from: 5-10 membered heteroaryl and 6-10 membered aryl, wherein Y is optionally substituted with 1-4 $Y^1$;

$Y^1$ is independently selected from: F, Cl, Br, I, $C_{1-6}$ alkyl, $C_{2-6}$ alkenyl, $C_{2-6}$ alkynyl, —$(CH_2)_nOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_a$ $OC(O)R^a$, —$(CH_2)_aCONR^aR^a$, $CF_3$, and $OCF_3$;

a is independently selected from the group consisting of 0, 1, and 2;

n is independently selected from: 1, 2, and 3;

p is independently selected from: 0, 1, and 2;

q is independently selected from 1, 2, 3, and 4; and, r is independently selected from 0, 1, 2, and 3.

In another embodiment, the present invention provides novel compounds, wherein the compound is of formula II or a stereoisomer or a pharmaceutically acceptable salt thereof:

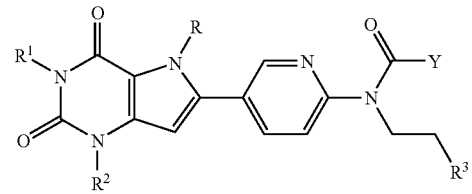

II wherein:

R is selected from: H and $C_{1-4}$ alkyl;

$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl) $C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;

$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle independently are optionally substituted with 1-2 $R^{3c}$;

$R^{3a}$ and $R^{3b}$ are independently selected from: $C_{1-4}$ alkyl, phenyl, and benzyl;

$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

Y is selected from: 5-6 membered heteroaryl and phenyl, wherein Y is optionally substituted with 1-2 $Y^1$;

$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and, $R^a$ is independently selected from: H, $C_{1-4}$ alkyl, $C_{3-6}$ cycloalkyl, phenyl, and benzyl.

In another embodiment, the present invention provides novel compounds, wherein:

R is H;

$R^1$ and $R^2$ are independently selected from: n-propyl, cyclopropylmethyl, and cyclobutyl;

$R^3$ is selected from: cyclopropyl, cyclobutyl, N-pyrrolidino, N-piperidino, N-piperazino, and N-morpholino;

Y is selected from: pyridyl and pyrimidyl, wherein Y optionally is substituted with 1-2 $Y^1$; and, $Y^1$ is independently selected from: F, Cl, $CH_3$, $OCH_3$, $NO_2$, —CN, and $CF_3$.

In another embodiment, the present invention provides novel compounds, wherein:

$R^1$ is selected from: n-propyl and cyclopropylmethyl; and, $R^2$ is n-propyl.

In another embodiment, the present invention provides novel compounds, wherein:

$R^1$ is n-propyl; and, $R^2$ is n-propyl.

In another embodiment, the present invention provides novel compounds, wherein the compound is of formula IV or a stereoisomer or a pharmaceutically acceptable salt thereof:

IV

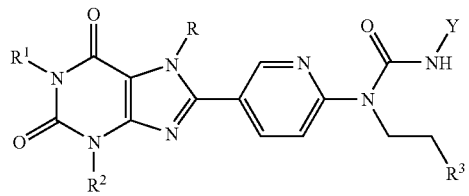

wherein:

R is selected from: H and $C_{1-4}$ alkyl;

$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl)$C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;

$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle independently are optionally substituted with 1-2 $R^{3c}$;

$R^{3a}$ and $R^{3b}$ are independently selected from: $C_{1-4}$ alkyl, phenyl, and benzyl;

$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

Y is selected from: 5-6 membered heteroaryl and phenyl, wherein Y is optionally substituted with 1-2 $Y^1$;

$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and, $R^a$ is independently selected from: H, $C_{1-4}$ alkyl, $C_{3-6}$ cycloalkyl, phenyl, and benzyl.

In another embodiment, the present invention provides novel compounds, wherein the compound is of formula V or VI or a stereoisomer or a pharmaceutically acceptable salt thereof:

V

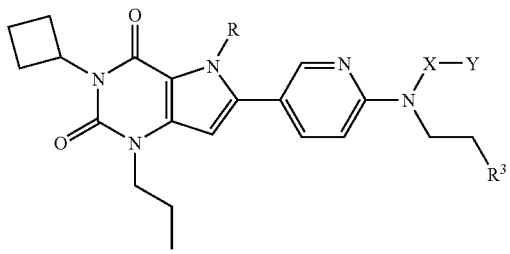

VI

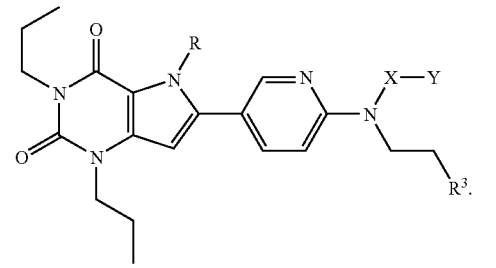

In another embodiment, the present invention provides novel compounds, wherein the compound is:

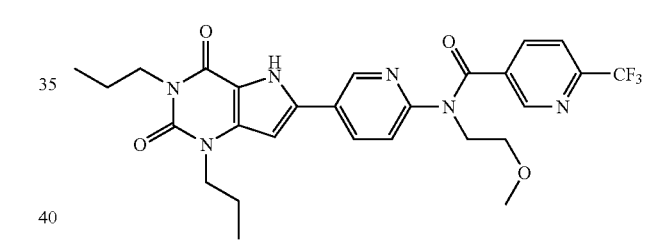

or a pharmaceutically acceptable salt thereof.

In another embodiment, the present invention provides novel compounds, wherein the compound is selected from Examples 1-396 of Table 1 or Examples 1-396 of Table 2 or a pharmaceutically acceptable salt thereof.

In another embodiment of the invention, there is provided a pharmaceutical composition, comprising: (a) a therapeutically effective amount of a compound of the present invention; and (b) a pharmaceutically acceptable excipient.

In another embodiment of the invention, there is provided a therapeutic method for treating a pathological condition or symptom in a mammal, wherein the activity of adenosine $A_{2B}$ receptors is implicated and antagonism of its action is desired, comprising administering to the mammal a therapeutically effective amount of a compound of the present invention.

In another embodiment of the invention, there is provided a method of treating a disease comprising administering a therapeutically effective amount of at least one compound of the present invention or a stereoisomer or pharmaceutically acceptable salt thereof, wherein the disease is selected from asthma, allergies, allergic diseases (e.g., allergic rhinitis and sinusitis), autoimmune diseases (e.g., lupus), pulmonary fibrosis, diarrheal diseases, insulin resistance, diabetes, obesity, prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy.

In another embodiment of the invention, there is provided the compound of the present invention for use in medical therapy.

In another embodiment, there is provided a use of a compound of the invention, for the manufacture of a medicament useful for the treatment of a disease in a mammal.

Any embodiment or feature of the present invention whether characterized as preferred or not characterized as preferred may be combined with any other aspect or feature of the invention, whether such other feature is characterized as preferred or not characterized as preferred.

DEFINITIONS

The examples provided in this application are non-inclusive unless otherwise stated. They include but are not limited to the recited groups.

The indefinite articles "a" and "an" mean "at least one" or "one or more" when used in this application, including the claims, unless specifically indicated otherwise.

Examples of the molecular weight of compounds of the present invention can include (a) less than about 500, 550, 600, 650, 700, 750, 800, 850, 900, 950, or 1000 grams per mole; (b) less than about 950 grams per mole; (c) less than about 850 grams per mole, and, (d) less than about 750 grams per mole.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The term "substituted" means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

Stable means that the compound is suitable for pharmaceutical use.

The present invention covers stable compound and thus avoids, unless otherwise specified, the following bond types: heteroatom-halogen, N—S, O—S, O—O, and S—S.

The present invention includes all isotopes of atoms occurring in the present compounds. Isotopes include those atoms having the same atomic number but different mass numbers. Isotopes of hydrogen include tritium and deuterium. Isotopes of carbon include C-13 and C-14.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups. Cycloalkyl also include bicycloalkyl and tricycloalkyl, both of which include fused and bridged rings (e.g., norbornane and adamantane).

"Halo" or "halogen" refers to fluoro, chloro, bromo, and iodo.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, and tetrahydronaphthyl.

"Heteroaryl" refers to any stable 5, 6, 7, 8, 9, 10, 11, or 12 membered, (unless the number of members is otherwise recited), monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl is defined by the number of carbons atoms, then 1, 2, 3, or 4 of the listed carbon atoms are replaced by a heteroatom. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

Examples of heteroaryl include acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Heterocycle" refers to any stable 4, 5, 6, 7, 8, 9, 10, 11, or 12 membered, (unless the number of members is otherwise recited), monocyclic, bicyclic, or tricyclic heterocyclic ring that is saturated or partially unsaturated, and which consists of carbon atoms and 1, 2, 3, or 4 heteroatoms independently selected from the group consisting of N, O, and S. If the heterocycle is defined by the number of carbons atoms, then from 1, 2, 3, or 4 of the listed carbon atoms are replaced by a heteroatom. If the heterocycle is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms optionally may be oxidized (e.g., S, S(O), S(O)$_2$, and N—O). The heterocycle may be attached to its pendant group at any heteroatom or carbon atom that results in a stable structure. The heterocycles described herein may be substituted on carbon or on a nitrogen atom if the resulting compound is stable.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Mammal and patient covers warm blooded mammals that are typically under medical care (e.g., humans and domesticated animals). Examples of mammals include (a) feline, canine, equine, and bovine and (b) human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting its development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

Obesity is defined based upon body mass index (BMI). A subject is obese if they have a BMI approximately over 30 and is severely obese if their BMI is approximately over 40.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1, 2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat obesity or another indication listed herein. "Therapeutically effective amount" also includes an amount of the combination of compounds claimed that is effective to treat the desired indication. The combination of compounds preferably is a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased effect, or some other beneficial effect of the combination compared with the individual components.

The compounds of the present invention may have a chiral center and may exist in and be isolated in optically active and racemic forms. Some compounds may exhibit polymorphism. The present invention encompasses any racemic, optically-active, polymorphic, or stereoisomeric form, or mixtures thereof, of a compound of the invention, which possess the useful properties described herein; it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine therapeutic activity using the standard tests described herein or using other similar tests which are well known in the art.

Specific and preferred values listed for radicals, substituents, and ranges, are for illustration only; they do not exclude other defined values or other values within defined ranges for the radicals and substituents.

Dosage and Formulation

The compounds of the present invention can be formulated as pharmaceutical compositions and administered to a mammalian host, such as a human patient, in a variety of forms adapted to the chosen route of administration, e.g., orally or parenterally, by intravenous, intramuscular, topical, inhalation or subcutaneous routes. Exemplary pharmaceutical compositions are disclosed in "Remington: The Science and Practice of Pharmacy", A. Gennaro, ed., 20th edition, Lippincott, Williams & Wilkins, Philadelphia, Pa.

The present compounds may be systemically administered, e.g., orally, in combination with a pharmaceutically acceptable excipient such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from (a) about 0.1-25 wt % and (b) about 0.5-10 wt %. The concentration in a semi-solid or solid composition such as a gel or a powder will be (a) about 0.1-5 wt % and (b) about 0.5-2.5 wt %.

The amount of the compound or an active salt or derivative thereof, required for use in treatment will vary not only with the particular compound or salt selected but also with the route of administration, the nature of the condition being treated, and the age and condition of the patient and will be ultimately at the discretion of the attendant physician or clinician. In general, however, a suitable dose will be in the range of from (a) about 1.0-100 mg/kg of body weight per day, (b) about 10-75 mg/kg of body weight per day, and (c) about 5-20 mg per kilogram body weight per day.

The compound can be conveniently administered in unit dosage form; e.g., tablets, caplets, etc., containing (a) about 4-400 mg, (b) about 10-200 mg, and (c) about 20-100 mg of active ingredient per unit dosage form.

Ideally, the active ingredient should be administered to achieve peak plasma concentrations of the active compound of from (a) about 0.02-20 µM, (b) about 0.1-10 µM, and (c) about 0.5-5 µM. These concentrations may be achieved, for example, by the intravenous injection of a 0.005-0.5% solution of the active ingredient, or orally administered as a bolus containing about 4-400 mg of the active ingredient.

The compounds of the invention can also be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail.

The invention has been described with reference to various specific and preferred embodiments and techniques. However, it should be understood that many variations and modifications may be made while remaining within the spirit and scope of the invention. The present invention, thus generally described, will be understood more readily by reference to the following examples, which are provided by way of illustration and are not intended to be limiting of the present invention.

EXAMPLES

Pharmacology.

The ability of compounds of the invention to act as an $A_{2B}$ adenosine receptor antagonists may be determined using pharmacological models which are well known to the art or using test procedures described below.

The rat $A_{2B}$ receptor cDNA was subcloned into the expression plasmid pDoubleTrouble using techniques described in Robeva, A. et al., *Biochem. Pharmacol.* 1996, 51, 545-555. The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA* 1987, 84, 7413-7417.

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioliganid Binding Studies.

At $A_{2B}$ receptors: Confluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenylmethanesulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.* 1978, 85, 572-580.

Saturation binding assays for rat $A_{2B}$ adenosine receptors were performed with [$^3$H]ZM214,385 (17 Ci/mmol, Tocris Cookson, Bristol UK) (Ji, X. et al., *Drug Design Discov.* 1999, 16, 216-226) or $^{125}$I-ABOPX (2200 Ci/mmol). To prepare $^{125}$I-ABOPX, 10 µL of 1 mM ABOPX in methanol/1 M NaOH (20:1) was added to 50 µL of 100 mM phosphate buffer, pH 7.3. One or 2 mCi of Na$^{125}$I was added, followed by 10 µL of 1 mg/mL chloramine-T in water. After incubation, 20 minutes at room temperature, 50 µL of 10 mg/mL Na-metabisulfite in water was added to quench the reaction. The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial $^{125}$I.

In equilibrium binding assays the ratio of $^{127}$I/$^{125}$I-ABOPX was 10-20/1. Radioligand binding experiments were performed in triplicate with 20-25 µg membrane protein in a total volume of 0.1 mL HE buffer supplemented with 1 U/mL adenosine deaminase and 5 mM $MgCl_2$. The incubation time was 3 h at 21° C. Nonspecific binding was measured in the presence of 100 µM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM $MgCl_2$, pH 7.4). $B_{max}$ and $K_D$ values were calculated by Marquardt's nonlinear least squares interpolation for single a site binding models. Marquardt, D. M., *J. Soc. Indust. Appl. Math.* 1963, 11, 431-441.21. K, values for different compounds were derived from $IC_{50}$ values as described. Linden, J., *J Cycl. Nucl. Res.* 1982, 8, 163-172. Data from replicate experiments are tabulated as means±SEM.

At other Adenosine Receptors: [$^3$H]CPX. Bruns, R. F. et al., *Naunyn-Schmiedeberg's Arch. Pharmacol.* 1987, 335, 59-63. $^{125}$I-ZM241385 and $^{125}$I-ABA were utilized in radioligand binding assays to membranes derived from HEK-293 cells expressing recombinant rat $A_1$, $A_{2A}$ and $A_3$ ARs, respectively. Binding of [$^3$H]R—N$^6$-phenylisopropyladenosine. Schwabe, U. et al., *Naunyn-Schmiedeberg's Arch. Pharmacol.* 1980, 313, 179-187. ([$^3$H]R-PIA, Amersham, Chicago, Ill.) to $A_1$ receptors from rat cerebral cortical membranes and of [$^3$H]CGS 21680. Jarvis, M. F. et al., *J. Pharmacol. Exp. Therap.* 1989, 251, 888-893. (Dupont NEN, Boston, Mass.) to $A_{2A}$ receptors from rat striatal membranes was performed as described. Adenosine deaminase (3 units/mL) was present during the preparation of the brain membranes, in a pre-incubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the $IC_{50}$ of each compound, were used. $IC_{50}$ values, calculated with the nonlinear regression method implemented in (Graph-Pad Prism, San Diego, Calif.), were converted to apparent $K_i$ values as described. Linden, J., *J. Cycl. Nucl. Res.* 1982, 8, 163-172. Hill coefficients of the tested compounds were in die range of 0.8 to 1.1.

Functional Assay:

HEK-$A_{2B}$ cells from one confluent T75 flask were rinsed with $Ca^{2+}$ and $Mg^{2+}$-free Dulbecco's phosphate buffered saline (PBS) and then incubated in $Ca^{2+}$ and $Mg^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM $MgSO_4$, 1.4 mM $CaCl_2$, 3 mM $NaHCO_3$, 0.6 mM $Na_2HPO_4$, 0.4 mM $KH_3PO_4$, 5.6 mM glucose, and 10 mM HEPES, pH 7.4 and the $Ca^{2+}$-sensitive fluorescent dye indo-1-AM (5 μM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 μL adenosine deaminase (final concentration 10 IU/mL) and 100 μL of solutions of rolipram and cilostamide (each at a final concentration of 10 μM) were added, followed by 50 μL of the test compound (appropriate concentration) or buffer. After 15 minutes, incubation at 37° C. was terminated by removing the medium and adding 200 μL of 0.1 M HCl. Acid extracts were stored at −20° C. until assay. The amounts of cyclic AMP were determined following a protocol which utilized a cAMP binding protein (PKA) [van der Wendell et al., 1995], with the following minor modifications. The assay buffer consisted of 150 mM $K_2HPO_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM $K_2HPO_4$/10 mM EDTA (pH 7.5, 4° C.). Punched filters were counted in Packard Emulsifier Safe scintillation fluid after 2 hours of extraction.

Representative compounds of the present invention have been shown to be active in the above affinity testing.

Synthesis and Characterization

Scheme I

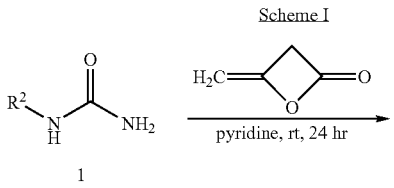

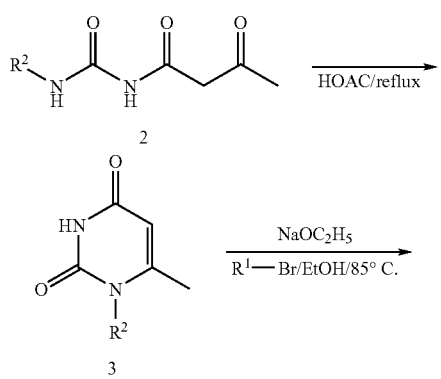

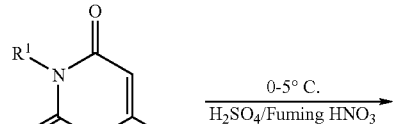

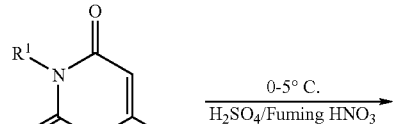

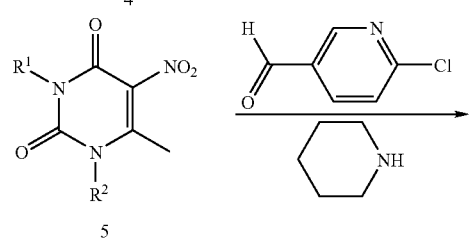

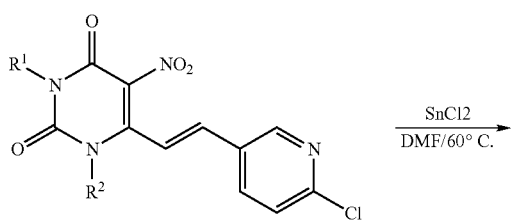

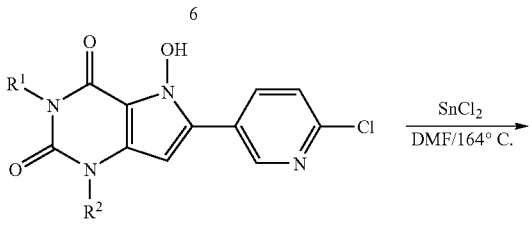

-continued

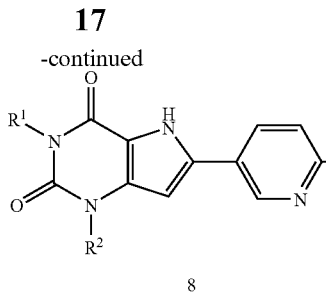

8

The compounds of Formula 8 can be prepared by the methods described by Bettina Grahner et al., *J. Med. Chem.* 1994, 37, 1526-1534 and Angela Stefanachi et al, *Tetrahedron Lett.* 2003, 44, 2121-2123, as shown above in Scheme I. Monosubstituted urea 1 reacts with diketene to afford compound 2, which is cyclized by refluxing in acetic acid to give compound 3. Compound 4 is prepared by 3-alkylation of compound 3. Nitration of 4 with $H_2SO_4$/fuming $HNO_3$ gives compound, which is condensed with 6-chloropyridine-3-carboxaldehyde in ethanol using piperidine as the base to give the vinyl compound 6. Compound 6 undergoes reductive cyclization in DMF by using $SnCl_2$ to afford 7, which can be further reduced to 8.

As shown above, compound 8 reacts with substituted amine at 160° C. in a pressure tube to give compound 9, which can react with acyl chloride to afford compounds of Formula 10. Compound 9 can also react with isocyanate to give compounds of Formular 11.

Proton nuclear magnetic resonance spectroscopy was performed on a Varian-300 MHz spectrometer and spectra were taken in DMSO-$d_6$. Unless noted, chemical shifts are expressed as ppm downfield from relative ppm from DMSO (2.5 ppm). Electro-spray-ionization (ESI) mass spectrometry was performed with a ThermoFinnigan LCQ mass spectrometer.

All compounds were homogeneous as judged using TLC (Silica gel 60 $F_{254}$, 0.25 mm, aluminium backed, EM Science, Gibbstown, N.J.) and HPLC (Shimadzu) using Varian C18 5 micron analytical column (4.6 mm×150 mm) in linear gradient solvent system, at a flow rate of 1 mL/min. The solvent system used was MeOH (0.1% formic acid):$H_2O$ (0.1% formic acid). Peaks were detected by UV absorption at 300 nm and 254 nm. NMR and mass spectra were shown to be consistent with the assigned structure.

Scheme II

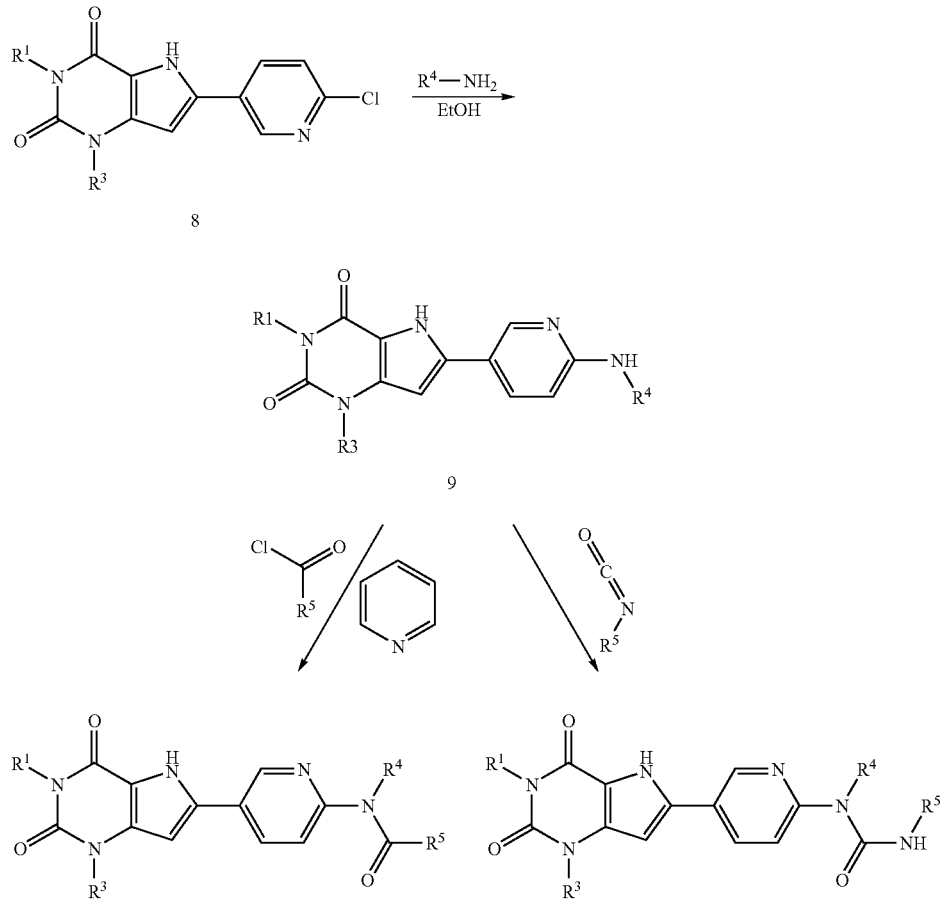

1-Propyl-3-(3-oxo-butyryl)-urea (2a)

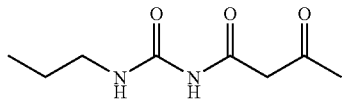

Diketene (2.6 mL, 33 mmol, reagent stabilized with CuSO$_4$), was added dropwise to a stirred solution of n-propylurea (3.06 g, 30 mmol) in pyridine (60 mL) at 0° C. (ice/water bath) under Ar. The resulting dark-yellow solution was stirred at rt for 24 hr. Most of the solvent was evaporated and the solid was collected by filtration and washed with ether and dried tinder vacuum to give the product (4.0 g).

HPLC condition: MeOH 20%-75% gradient in 10 minutes then MeOH 75%. Retention Time=7.00 min. MS: m/z 187 (M+H)$^+$.

1-Propyl-6-methyl-uracil (3a)

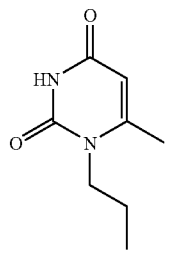

The acyl urea (2a) (3.2 g) was suspended in acetic acid (30 mL) and the mixture was stirred under reflux for 2 hr. Most of the solvent was evaporated and the solid was stirred with water (20 mL) and filtered to give the product (2.5 g). \

HPLC condition: MeOH 20%-75% gradient in 10 minutes then MeOH 75%. Retention Time=5.72 min. $^1$H NMR (DMSO, d$_6$): 0.87 (t, 3H, J=7.5 Hz), 1.55 (m, 2H), 2.23 (s, 3H), 3.65 (t, 2H, J=7.5 Hz), 5.47 (s, 1H), 11.13 (s, 1H). $^{13}$C NMR (DMSO, d$_6$): 11.61, 11.87, 22.28, 45.55, 101.67, 152.25, 154.89, 163.18. MS: m/z 169 (M+H)$^+$.

1,3-Dipropyl-6-methyl-uracil (4a)

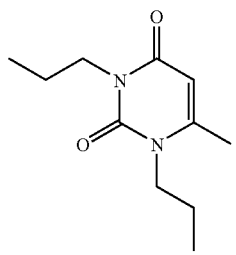

Method A: 1-Propyl-6-methyluracil (4.5 g) was dissolved in NaOEt solution (from 850 mg of Na and 60 mL of absolute EtOH) in a pressure tube. After 30 min, n-propyl bromine (5 g) was added. The mixture was stirred at 85° C. for 24 hr. HPLC indicated that the reaction was only 40% complete. More n-propyl bromine (3 g) was added. The mixture was sealed and stirred at 87° C., for another 24 hr. HPLC indicated that there was 20% of the starting material left. Additional n-propyl bromine (3 g) was added. The reaction was continued at 87° C. for another 24 h. EtOH was removed and residue was dissolved in water and neutralized with 1N HCl and extracted with dichloromethane (DCM). DCM was evaporated and the crude product was purified by column (43 g silica gel, RT Scientific) (CH$_2$Cl$_2$:MeOH=100:0 to 98:2).

HPLC condition: MeOH 20%-75% gradient in 10 minutes then MeOH 75%. Retention Time=10.23 min. $^1$H NMR (DMSO, d$_6$): 0.85 (m, 6H), 1.46-1.61 (m, 4H), 2.25 (s, 3H), 3.72 (m, 4H), 5.60 (s, 1H). $^{13}$C NMR (DMSO, d$_6$): 11.61, 11.86, 19.77, 21.15, 22.19, 42.46, 46.59, 100.97, 152.25, 153.28, 162.04. MS: m/z 211 (M+H).

Method B: 6-Methyluracil (25.2 g), dry K$_2$CO$_3$ (55.2 g) was suspended in DMF (400 mL) in a pressure tube. n-C$_3$H$_7$—Br (49 g) was added. The mixture was stirred at 65-70° C. for 3 days. Solid was removed by filtration. The mother liquid was evaporated, and the residue was purified by column to give the product (24 g). (170 g silica gel, RT Scientific) (CH$_2$Cl$_2$:MeOH=100:0 to 98:2) and byproducts, mixture 1-propyl-6-methyluracil (Retention Time=5.82 min) and 3-propyl-6-methyluracil (Retention Time=6.65 min) (6.5 g). The product has a high solubility in ether and can be recrystallized from hexane while 1-propyl-6-methyluracil and 3-propyl-6-methyluracil have a low solubility in ether.

HPLC condition: MeOH 20%-75% gradient in 10 minutes then MeOH 75%. Retention Time=10.23 min. $^1$H NMR (DMSO, d$_6$): 0.85 (m, 6H), 1.46-1.61 (m, 4H), 2.25 (s, 3H), 3.72 (m, 4H), 5.60 (s, 1H). $^{13}$C NMR (DMSO, d$_6$): 11.61, 11.86, 19.77, 21.15, 22.19, 42.46, 46.59, 100.97, 152.25, 153.28, 162.04. MS: m/z 211 (M+H).

1,3-Dipropyl-5-nitro-6-methyl-uracil (5a)

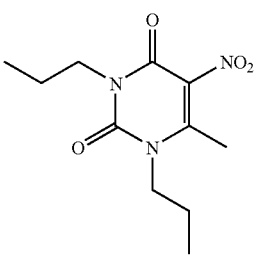

1,3-Dipropyl 6-methyluracil (13.65 g) was added the cold mixture of H$_2$SO$_4$/HNO$_3$ [concentrated H$_2$SO$_4$ (30 mL)+ fuming HNO$_3$ (20 mL)]. The mixture was stirred at 0-5° C. for 1.5 hr. The mixture was poured into ice and neutralized with saturated NaHCO$_3$ and extracted with DCM. DCM was evaporated, and the crude product was purified by column (170 g silica gel, RT Scientific) (CH$_2$Cl$_2$:MeOH=100:0 to 99:1) to give the product (yellow oil, 15.3 g).

HPLC condition: MeOH 20%-75% gradient in 10 minutes then MeOH 75%. Retention Time=10.55 min. $^1$H NMR (DMSO, d$_6$): 0.99 (m, 6H), 1.71 (m, 4H), 2.52 (s, 3H), 3.92 (m, 4H), 5.60 (s, 1H). $^{13}$C NMR (DMSO, d$_6$): 11.65, 11.91, 16.24, 20.97, 21.90, 43.88, 47.87, 130.16, 150.33, 151.30, 155.52. MS: m/z 256 (M+H).

1,3-Dipropyl-5-nitro-6-(2-(6-chloropyridin-3-yl)vinyl)-uracil (6a)

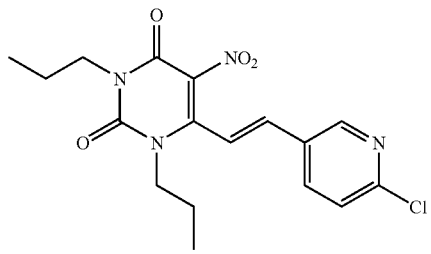

6a

A mixture of 1,3-dipropyl-5-nitro-6-methyluracil (2.55 g), 6-chloropyridine-3-carboxaldehyde (1.60 g), piperidine (1.58 mL), and dry dioxane (50 mL) in a pressure tube was stirred at 110° C. for 23 hr. HPLC indicated only 60% of the starting material was converted to the unsaturated compound [HPLC condition: MeOH 20%-75% gradient in 10 minutes then MeOH 75%. Retention Time=12.44 min, MS: m/z 379 (M+H)]. The solvent was evaporated, and the residue was purified by column (115 g silica gel, RT Scientific) (Hexane:Ethyl Acetate=100:0 to 80:20). The fractions were evaporated and washed with ether to give the product (yellow solid, 600 mg).

HPLC condition: MeOH 20%-75% gradient in 10 minutes then MeOH 75%. Retention Time=12.44 min. $^1$H NMR (DMSO, $d_6$): 0.85 (m, 6H), 1.55-1.65 (m, 4H), 3.82 (t, 4H, J=7.5 Hz), 7.07 (d, 1H, J=16.5 Hz), 7.40 (d, 1H, J=16.5 Hz), 7.62 (d, 1H, J=8.7 Hz), 8.24 (dd, $J_1$=8.7 Hz, $J_2$=2.4 Hz), 8.65 (d, 1H, J=2.4 Hz). $^{13}$C NMR (DMSO, $d_6$): 11.66, 11.96, 20.98, 21.93, 44.07, 48.59, 118.94, 125.45, 129.43, 130.47, 135.67, 138.60, 149.52, 150.11, 150.29, 152.02, 155.82. MS: m/z 379 (M+H).

6-(6-chloropyridin-3-yl)-1,3-dipropyl-5-hydroxy-1H-pyrrolo[3,2-d]pyrimidine-2,4(3H,5H)-dione (7a)

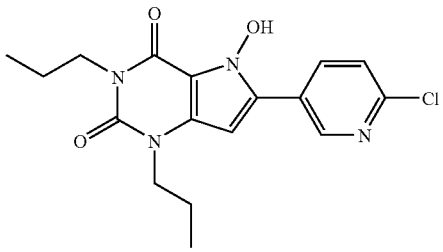

7a

The vinyl compound 6a (300 mg), was dissolved in dry DMF (6 mL) in a pressure tube. $SnCl_2$ (1500 mg) was added and the pressure was sealed and stirred at 60° C. for 4 hr. LCMS, indicated the desired 7-N-hydroxy-9-deazaxanthine product 7a (rt=9.49 min) and deoxygenated product 8a (rt=10.15, m/z 347). The solvent was evaporated, and the residue was purified by column (dry loaded, 45 g silica gel, RT Scientific) ($CH_2Cl_2$:MeOH=100:0 to 99:1). The fractions were evaporated and washed with water and ether to give the mixture of those two products (100 mg).

HPLC condition: MeOH 40%-95% gradient in 10 minutes then MeOH 95%. Retention Time=9.49 min and 10.15 min.

6-(6-chloropyridin-3-yl)-1,3-dipropyl-1H-pyrrolo[3,2-d]pyrimidine-2,4(3H,5H)-dione (8a)

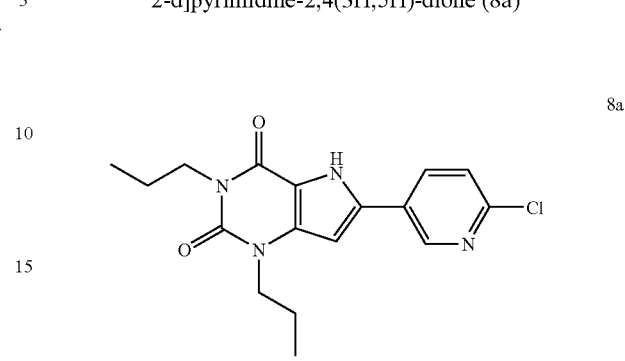

8a

A mixture of 7a and 8a (100 mg) from last step and $SnCl_2$ (545 mg) in DMF (5 mL) in a pressure tube was stirred at 164° C. for 24 hr. HPLC indicated the reaction was complete. The solvent was evaporated, and the residue was stirred with water (20 mL) and filtered. The crude solid was purified by column (dry loaded, 14 g silica gel, RT Scientific) ($CH_2Cl_2$:MeOH=100:0 to 99:1). The fractions were evaporated and washed with ether to give the product.

HPLC condition: MeOH 40%-95% gradient in 10 minutes then MeOH 95%. Retention Time=10.15 min. $^1$H NMR (DMSO, $d_6$): 0.89 (m, 6H), 1.53-1.72 (m, 4H), 3.86 (t, 4H, J=6.9 Hz), 6.95 (s, 1H), 7.61 (d, 1H, J=8.4 Hz), 8.35 (dd, $J_1$=8.4 Hz, $J_2$=2.4 Hz), 8.96 (d, 1H, J=2.4 Hz). $^{13}$C NMR (DMSO, $d_6$): 11.78, 11.99, 21.43, 21.73, 42.73, 47.25, 95.17, 112.73, 125.20, 127.20, 135.61, 136.11, 136.87, 147.58, 150.13, 151.34, 155.36. MS: m/z 347 (M+H).

6-(6-(2-methoxyethylamino)pyridin-3-yl)-1,3-dipropyl-1H-pyrrolo[3,2-d]pyrimidine-2,4(3H,5H)-dione (9a)

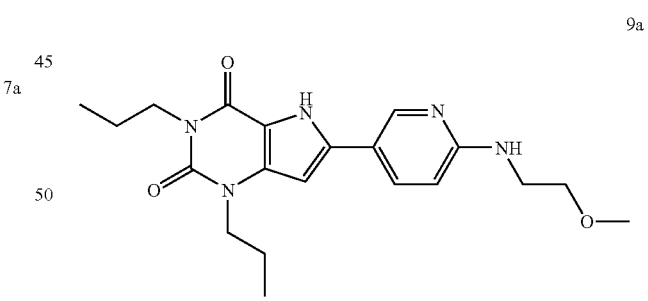

9a 8a (100 mg) was suspended in methoxyethylamine (1.5 g), in EtOH (4 mL) in a pressure tube and stirred at 164° C. for 28 hrs. After cooling to room temperature, the solvent was removed and the solid was purified by column (26 g silica gel, RT Scientific) ($CH_2Cl_2$:MeOH=100:0 to 97:3). The fractions were evaporated and washed with ether to give the product 9a (63 mg). The mother liquid was evaporated and afforded another 30 mg of the product.

HPLC condition: MeOH 40%-95% gradient in 10 minutes then MeOH 95%. Retention Time=6.57 min. $^1$H NMR (DMSO, $d_6$): 0.84-0.93 (m, 6H), 1.53-1.71 (m, 4H), 3.27 (s, 3H), 3.46 (m, 4H), 3.85 (m, 4H), 6.54 (m, 2H), 6.90 (s(br), 1H), 7.86 (dd, 1H, J₁=8.7 Hz, J₂=2.4 Hz), 8.54 (d, 1H, J=2.4 Hz), 12.10 (s, 1H). ¹³C NMR (DMSO, d₆): 11.00, 11.20, 20.67, 21.00, 40.34, 41.76, 46.33, 57.99, 70.88, 90.94, 108.07, 109.97, 115.14, 134.02, 135.83, 138.64, 145.42, 150.69, 154.14, 158.38.

6-(Trifluoromethyl)-N-(5-(2,3,4,5-tetrahydro-2,4-dioxo-1,3-dipropyl-1H-pyrrolo[3,2-d]pyrimidin-6-yl)pyridin-2-yl)-N-(2-methoxyethyl)pyridin-3-carboxamide (10a)

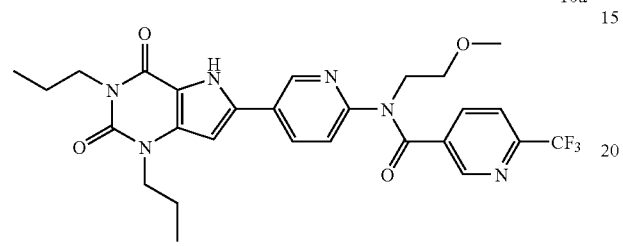

9a (40 mg) was dissolved in pyridine (5 mL) at room temperature. 6-(Trifluoromethyl)nicotinoyl chloride (218 mg) was added. The mixture was stirred at room temperature for 24 h. After quenching with ice, the crude product was purified by column (26 g silica gel, RT Scientific) (CH₂Cl₂: MeOH=100:0 to 98:2) to give the 10a (43 mg).

HPLC condition: MeOH 40%-95% gradient in 10 minutes then MeOH 95%. Retention Time=10.21 min. ¹H NMR (DMSO, d₆): 0.83-0.92 (m, 6H), 1.53-1.70 (m, 4H), 3.20 (s, 3H), 3.61 (t, 2H, J=5.7 Hz), 3.85 (m, 4H), 4.19 (t, 2H, J=5.7 Hz), 6.89 (d, 1H, J=2.4 Hz), 7.41 (d, 1H, J=8.7 Hz), 7.84-7.95 (m, 2H), 8.26 (dd, 1H, J₁=8.7 Hz, J₂=2.4 Hz), 8.65 (s, 1H), 8.85 (d, 1H, J=2.4 Hz), 12.52 (s, 1H). ¹³C NMR (DMSO, d₆): 10.94, 11.17, 20.60, 20.92, 41.91, 46.41, 47.50, 58.09, 69.52, 94.06, 111.75, 120.41, 120.86, 123.06, 124.90, 134.74, 135.24, 135.35, 135.74, 137.79, 145.36, 146.49, 149.11, 150.56, 154.00, 154.49, 166.80. MS: m/z 559 (M+H)⁺.

6-(6-((Tetrahydrofuran-2-yl)methylamino)pyridin-3-yl)-1,3-dipropyl-1H-pyrrolo[3,2-d]pyrimidine-2,4(3H,5H)-dione (9b)

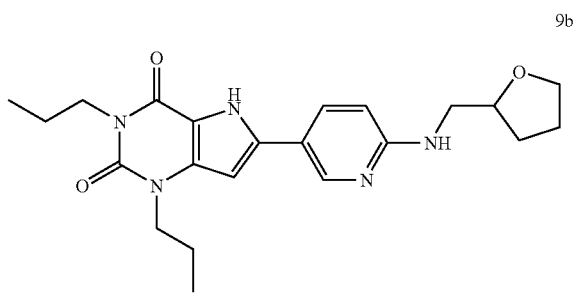 [SMILES: CCCn1c(=O)c2[nH]c(-c3ccc(NCC4CCCO4)nc3)cc2n(CCC)c1=O]

8a (154 mg) was suspended in tetrahydrofurfurylamine (2.0 g) in EtOH (5 ml) in a pressure tube and stirred at 164° C. for 5 days. After cooling to room temperature, the solid was filtered and washed with methanol to give the product (9b) (150 mg).

HPLC condition: MeOH 40%-95% gradient in 10 minutes then MeOH 95%. Retention Time=7.1 min. ¹H NMR (DMSO, d₆): 0.83-0.93 (m, 6H), 1.53-2.00 (m, 8H), 3.40 (m, 2H), 3.59-3.99 (m, 7H), 6.54 (s, 1H), 6.57 (d, 1H, J=8.7 Hz), 6.92 (t, 1H, J=5.4 Hz), 7.85 (dd, 1H, J₁=8.7 Hz, J₂=2.4 Hz), 8.52 (d, 1H, J=2.4 Hz), 12.20 (s, 1H). MS: m/z 412 (M+H)⁺.

6-(6-(2-dimethylamino)ethylamino)pyridin-3-yl)-1,3-dipropyl-1H-pyrrolo[3,2-d]pyrimidine-2,4(3H,5H)-dione (9c)

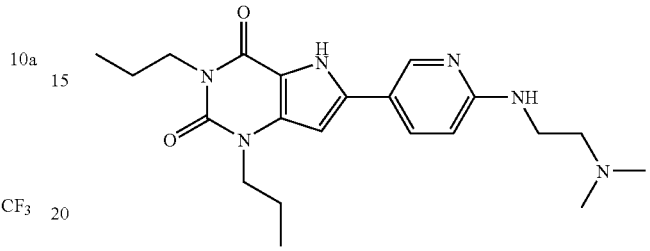

8a (135 mg) was suspended in N,N-dimethylethylenediamine (1.5 g) in EtOH (4 ml) in quartz tube and stirred at 160-175° C. under microwave (400 w) (CEM Mars) for 2 hrs. After cooling to room temperature, the solvent was removed and the solid was purified by column (26 g silica gel, RT Scientific) (CH₂Cl₂: MeOH=100:0 to 90:10). The fractions was evaporated and washed with ether to give the product (9c) (90 mg). HPLC condition: MeOH 40%-95% gradient in 10 minutes then MeOH 95%. Retention Time=5.32 min. ¹H NMR (DMSO, d₆): 0.83-0.93 (m, 6H), 1.53-1.71 (m, 4H), 2.21 (s, 6H), 2.45 (t, 2H, J=6.6 Hz), 3.38 (m, 2H), 3.85 (m, 4H), 6.55 (m, 2H), 6.73 (t, 1H, J=5.4 Hz), 7.86 (dd, 1H, J₁=8.7 Hz, J₂=2.4 Hz), 8.54 (d, 1H, J=2.4 Hz), 12.22 (s, 1H). MS: m/z 399 (M+H)⁺.

3-(4-fluorophenyl)-1-(5-(2,3,4,5-tetrahydro-2,4-dioxo-1,3-dipropyl-1H-pyrrolo[3,2-d]pyrimidin-6-yl)pyridin-2-yl)-1-(2-methoxyethyl)urea (11a)

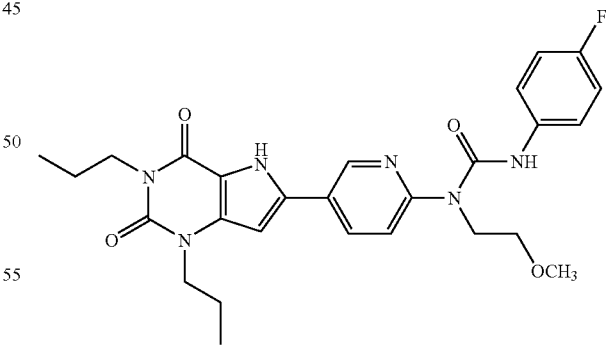

9a (25 mg) was suspended in THF (2 ml) in a pressure tube, 4-fluorophenyl isocyanate (200 mg) was added and the mixture was stirred at 94° C. for 3 days. After cooling to room temperature, the mixture was evaporated to almost dry and the solid was filtered and washed with ether (two peaks shown in HPLC, rt=8.0 min, rt=1.6 min). The solid was stirred with DCM, the solid (rt=8.0 min) was removed and the mother liquid was collected. After removal of the solvent, the residue was purified by column (14 g silica gel, RT Scientific)

(CH$_2$Cl$_2$: MeOH=100:0 to 98:2) to give the product (11a) (9 mg). HPLC condition: MeOH 40%-95% gradient in 10 minutes then MeOH 95%. Retention Time=11.60 min. $^1$H NMR (DMSO, d$_6$): 0.83-0.95 (m, 6H), 1.53-1.75 (m, 4H), 3.26 (s, 3H), 3.60 (t, 2H), 3.87 (t, 2H), 4.17 (t, 2H), 6.85 (s, 1H), 7.16 (t, 2H, J=8.7 Hz), 7.48 (m, 3H), 8.30 (dd, 1H, J$_1$=8.7 Hz, J$_2$=2.4 Hz), 8.95 (d, 1H, J=2.4 Hz), 10.87 (s, 1H), 12.50 (s, 1H). MS: m/z 523 (M+H)$^+$.

3-(4-fluorophenyl)-1-(5-(2,3,4,5-tetrahydro-2,4-dioxo-1,3-dipropyl-1H-pyrrolo[3,2-d]pyrimidin-6-yl)pyridin-2-yl)-1-((tetrahydrofuran-2-yl)methyl)urea (11b)

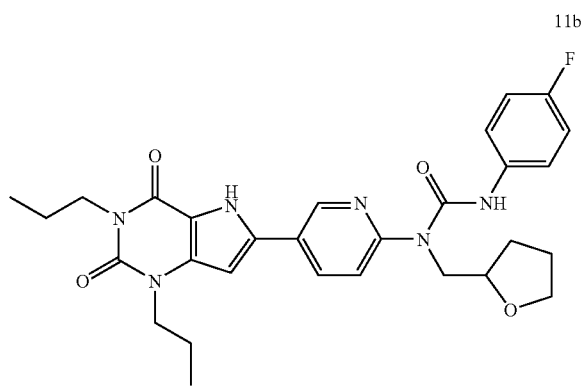 [SMILES: CCCn1c(=O)c2[nH]c(-c3ccc(N(CC4CCCO4)C(=O)Nc4ccc(F)cc4)nc3)cc2n(CCC)c1=O]

9b (30 mg) was suspended in THF (2 ml) in a pressure tube, 4-fluorophenyl isocyanate (300 mg) was added and the mixture was stirred at 94° C. for 3 days. After cooling to room temperature, the mixture was evaporated to almost dry and the solid was filtered, washed with ether and purified by column (14 g silica gel, RT Scientific) (CH$_2$Cl$_2$: MeOH=100:0 to 98:2) to give the product (11b) (18 mg). HPLC condition: MeOH 40%-95% gradient in 10 minutes then MeOH 95%. Retention Time=11.60 min. $^1$H NMR (DMSO, d$_6$): 0.83-0.95 (m, 6H), 1.53-2.00 (m, 8H), 3.60-4.20 (m, 9H), 6.85 (s, 1H), 7.15 (t, 2H, J=8.7 Hz), 7.51 (m, 3H), 8.30 (dd, 1H, J$_1$=8.7 Hz, J$_2$=2.4 Hz), 8.94 (d, 1H, J=2.4 Hz), 10.69 (s, 1H), 12.50 (s, 1H). MS: m/z 549 (M+H)$^+$.

1-(2-(dimethylamino)ethyl)-3-(4-fluorophenyl)-1-(5-(2,3,4,5-tetrahydro-2,4-dioxo-1,3-dipropyl-1H-pyrrolo[3,2-d]pyrimidin-6-yl)pyridin-2-yl)urea (11c)

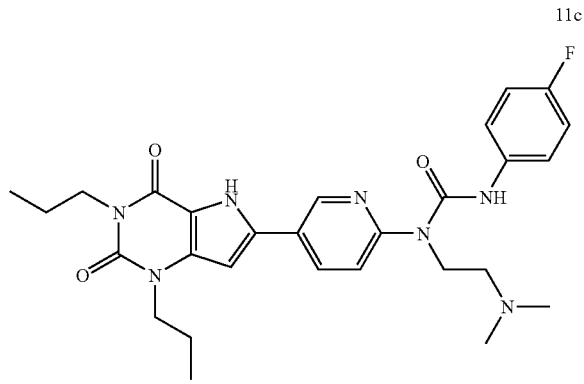 [SMILES: CCCn1c(=O)c2[nH]c(-c3ccc(N(CCN(C)C)C(=O)Nc4ccc(F)cc4)nc3)cc2n(CCC)c1=O]

9c (35 mg) was suspended in THF (3 ml) in a pressure tube, 4-fluorophenyl isocyanate (130 mg) was added and the mixture was stirred at 85° C. for 3 days. After cooling to room temperature, the mixture was evaporated and the solid was stirred with ether and filtered The mother liquid contained most of the product. After removal of the solvent, the residue was purified by column (14 g silica gel, RT Scientific) (CH$_2$C$_2$: MeOH=100:0 to 95:5) to give the product (11c) (22 mg). HPLC condition: MeOH 40%-95% gradient in 10 minutes then MeOH 95%. Retention Time=7.20 min. $^1$H NMR (DMSO, d$_6$): 0.83-0.93 (m, 6H), 1.53-1.71 (m, 4H), 2.28 (s, 6H), 2.50 (s, 4H), 3.87 (m, 4H), 4.14 (t, 1H, J=5.4 Hz), 6.83 (s, 1H), 7.15 (t, 2H, J=8.7 Hz), 7.52 (m, 3H), 8.24 (dd, 1H, J$_1$=8.7 Hz, J$_2$=2.4 Hz), 8.92 (d, 1H, J=2.4 Hz), 11.54 (s, 1H). MS: m/z 536 (M+H)$^+$.

Representative examples of the present invention are provided below in Tables 1-2.

TABLE 1

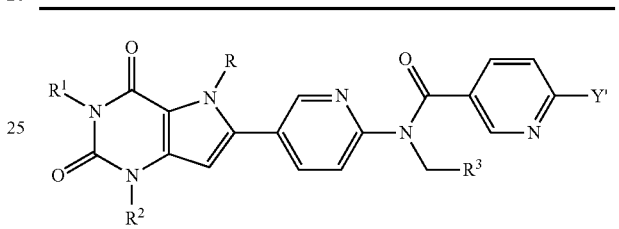

| Ex. # | R | R$^1$ | R$^2$ | R$^3$ | Y' |
|---|---|---|---|---|---|
| 1. | H | n-propyl | n-propyl | CH$_2$OCH$_3$ | H |
| 2. | H | n-propyl | n-propyl | CH$_3$ | H |
| 3. | H | n-propyl | n-propyl | CH$_2$OH | H |
| 4. | H | n-propyl | n-propyl | CH$_2$N(CH$_3$)$_2$ | H |
| 5. | H | n-propyl | n-propyl | CH$_2$—N-piperidinyl | H |
| 6. | H | n-propyl | n-propyl | CH$_2$—N-morpholinyl | H |
| 7. | H | n-propyl | n-propyl | cyclopropyl | H |
| 8. | H | n-propyl | n-propyl | CH$_2$-cyclopropyl | H |
| 9. | H | n-propyl | n-propyl | 2-tetrahydrofuranyl | H |
| 10. | H | n-propyl | n-propyl | CH$_2$-2-tetrahydrofuran | H |
| 11. | H | n-propyl | n-propyl | 2-tetrahydrothienyl | H |
| 12. | H | n-propyl | n-propyl | CH$_2$OCH$_3$ | CF$_3$ |
| 13. | H | n-propyl | n-propyl | CH$_3$ | CF$_3$ |
| 14. | H | n-propyl | n-propyl | CH$_2$OH | CF$_3$ |
| 15. | H | n-propyl | n-propyl | CH$_2$N(CH$_3$)$_2$ | CF$_3$ |
| 16. | H | n-propyl | n-propyl | CH$_2$—N-piperidinyl | CF$_3$ |
| 17. | H | n-propyl | n-propyl | CH$_2$—N-morpholinyl | CF$_3$ |
| 18. | H | n-propyl | n-propyl | cyclopropyl | CF$_3$ |
| 19. | H | n-propyl | n-propyl | CH$_2$-cyclopropyl | CF$_3$ |
| 20. | H | n-propyl | n-propyl | 2-tetrahydrofuranyl | CF$_3$ |
| 21. | H | n-propyl | n-propyl | CH$_2$-2-tetrahydrofuran | CF$_3$ |
| 22. | H | n-propyl | n-propyl | 2-tetrahydrothienyl | CF$_3$ |
| 23. | H | n-propyl | n-propyl | CH$_2$OCH$_3$ | F |
| 24. | H | n-propyl | n-propyl | CH$_3$ | F |
| 25. | H | n-propyl | n-propyl | CH$_2$OH | F |
| 26. | H | n-propyl | n-propyl | CH$_2$N(CH$_3$)$_2$ | F |
| 27. | H | n-propyl | n-propyl | CH$_2$—N-piperidinyl | F |
| 28. | H | n-propyl | n-propyl | CH$_2$—N-morpholinyl | F |
| 29. | H | n-propyl | n-propyl | cyclopropyl | F |
| 30. | H | n-propyl | n-propyl | CH$_2$-cyclopropyl | F |
| 31. | H | n-propyl | n-propyl | 2-tetrahydrofuranyl | F |
| 32. | H | n-propyl | n-propyl | CH$_2$-2-tetrahydrofuran | F |
| 33. | H | n-propyl | n-propyl | 2-tetrahydrothienyl | F |
| 34. | H | n-propyl | n-propyl | CH$_2$OCH$_3$ | Cl |
| 35. | H | n-propyl | n-propyl | CH$_3$ | Cl |
| 36. | H | n-propyl | n-propyl | CH$_2$OH | Cl |
| 37. | H | n-propyl | n-propyl | CH$_2$N(CH$_3$)$_2$ | Cl |
| 38. | H | n-propyl | n-propyl | CH$_2$—N-piperidinyl | Cl |
| 39. | H | n-propyl | n-propyl | CH$_2$—N-morpholinyl | Cl |
| 40. | H | n-propyl | n-propyl | cyclopropyl | Cl |
| 41. | H | n-propyl | n-propyl | CH$_2$-cyclopropyl | Cl |
| 42. | H | n-propyl | n-propyl | 2-tetrahydrofuranyl | Cl |
| 43. | H | n-propyl | n-propyl | CH$_2$-2-tetrahydrofuran | Cl |
| 44. | H | n-propyl | n-propyl | 2-tetrahydrothienyl | Cl |

TABLE 1-continued

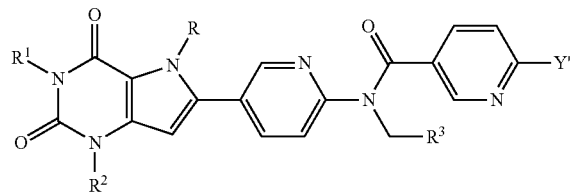

| Ex. # | R | R¹ | R² | R³ | Y' |
|---|---|---|---|---|---|
| 45. | H | n-propyl | n-propyl | CH$_2$OCH$_3$ | Br |
| 46. | H | n-propyl | n-propyl | CH$_3$ | Br |
| 47. | H | n-propyl | n-propyl | CH$_2$OH | Br |
| 48. | H | n-propyl | n-propyl | CH$_2$N(CH$_3$)$_2$ | Br |
| 49. | H | n-propyl | n-propyl | CH$_2$—N-piperidinyl | Br |
| 50. | H | n-propyl | n-propyl | CH$_2$—N-morpholinyl | Br |
| 51. | H | n-propyl | n-propyl | cyclopropyl | Br |
| 52. | H | n-propyl | n-propyl | CH$_2$-cyclopropyl | Br |
| 53. | H | n-propyl | n-propyl | 2-tetrahydrofuranyl | Br |
| 54. | H | n-propyl | n-propyl | CH$_2$-2-tetrahydrofuran | Br |
| 55. | H | n-propyl | n-propyl | 2-tetrahydrothienyl | Br |
| 56. | H | n-propyl | n-propyl | CH$_2$OCH$_3$ | I |
| 57. | H | n-propyl | n-propyl | CH$_3$ | I |
| 58. | H | n-propyl | n-propyl | CH$_2$OH | I |
| 59. | H | n-propyl | n-propyl | CH$_2$N(CH$_3$)$_2$ | I |
| 60. | H | n-propyl | n-propyl | CH$_2$—N-piperidinyl | I |
| 61. | H | n-propyl | n-propyl | CH$_2$—N-morpholinyl | I |
| 62. | H | n-propyl | n-propyl | cyclopropyl | I |
| 63. | H | n-propyl | n-propyl | CH$_2$-cyclopropyl | I |
| 64. | H | n-propyl | n-propyl | 2-tetrahydrofuranyl | I |
| 65. | H | n-propyl | n-propyl | CH$_2$-2-tetrahydrofuran | I |
| 66. | H | n-propyl | n-propyl | 2-tetrahydrothienyl | I |
| 67. | H | i-propyl | n-propyl | CH$_2$OCH$_3$ | H |
| 68. | H | i-propyl | n-propyl | CH$_3$ | H |
| 69. | H | i-propyl | n-propyl | CH$_2$OH | H |
| 70. | H | i-propyl | n-propyl | CH$_2$N(CH$_3$)$_2$ | H |
| 71. | H | i-propyl | n-propyl | CH$_2$—N-piperidinyl | H |
| 72. | H | i-propyl | n-propyl | CH$_2$—N-morpholinyl | H |
| 73. | H | i-propyl | n-propyl | cyclopropyl | H |
| 74. | H | i-propyl | n-propyl | CH$_2$-cyclopropyl | H |
| 75. | H | i-propyl | n-propyl | 2-tetrahydrofuranyl | H |
| 76. | H | i-propyl | n-propyl | CH$_2$-2-tetrahydrofuran | H |
| 77. | H | i-propyl | n-propyl | 2-tetrahydrothienyl | H |
| 78. | H | i-propyl | n-propyl | CH$_2$OCH$_3$ | CF$_3$ |
| 79. | H | i-propyl | n-propyl | CH$_3$ | CF$_3$ |
| 80. | H | i-propyl | n-propyl | CH$_2$OH | CF$_3$ |
| 81. | H | i-propyl | n-propyl | CH$_2$N(CH$_3$)$_2$ | CF$_3$ |
| 82. | H | i-propyl | n-propyl | CH$_2$—N-piperidinyl | CF$_3$ |
| 83. | H | i-propyl | n-propyl | CH$_2$—N-morpholinyl | CF$_3$ |
| 84. | H | i-propyl | n-propyl | cyclopropyl | CF$_3$ |
| 85. | H | i-propyl | n-propyl | CH$_2$-cyclopropyl | CF$_3$ |
| 86. | H | i-propyl | n-propyl | 2-tetrahydrofuranyl | CF$_3$ |
| 87. | H | i-propyl | n-propyl | CH$_2$-2-tetrahydrofuran | CF$_3$ |
| 88. | H | i-propyl | n-propyl | 2-tetrahydrothienyl | CF$_3$ |
| 89. | H | i-propyl | n-propyl | CH$_2$OCH$_3$ | F |
| 90. | H | i-propyl | n-propyl | CH$_3$ | F |
| 91. | H | i-propyl | n-propyl | CH$_2$OH | F |
| 92. | H | i-propyl | n-propyl | CH$_2$N(CH$_3$)$_2$ | F |
| 93. | H | i-propyl | n-propyl | CH$_2$—N-piperidinyl | F |
| 94. | H | i-propyl | n-propyl | CH$_2$—N-morpholinyl | F |
| 95. | H | i-propyl | n-propyl | cyclopropyl | F |
| 96. | H | i-propyl | n-propyl | CH$_2$-cyclopropyl | F |
| 97. | H | i-propyl | n-propyl | 2-tetrahydrofuranyl | F |
| 98. | H | i-propyl | n-propyl | CH$_2$-2-tetrahydrofuran | F |
| 99. | H | i-propyl | n-propyl | 2-tetrahydrothienyl | F |
| 100. | H | i-propyl | n-propyl | CH$_2$OCH$_3$ | Cl |
| 101. | H | i-propyl | n-propyl | CH$_3$ | Cl |
| 102. | H | i-propyl | n-propyl | CH$_2$OH | Cl |
| 103. | H | i-propyl | n-propyl | CH$_2$N(CH$_3$)$_2$ | Cl |
| 104. | H | i-propyl | n-propyl | CH$_2$—N-piperidinyl | Cl |
| 105. | H | i-propyl | n-propyl | CH$_2$—N-morpholinyl | Cl |
| 106. | H | i-propyl | n-propyl | cyclopropyl | Cl |
| 107. | H | i-propyl | n-propyl | CH$_2$-cyclopropyl | Cl |
| 108. | H | i-propyl | n-propyl | 2-tetrahydrofuranyl | Cl |
| 109. | H | i-propyl | n-propyl | CH$_2$-2-tetrahydrofuran | Cl |
| 110. | H | i-propyl | n-propyl | 2-tetrahydrothienyl | Cl |
| 111. | H | i-propyl | n-propyl | CH$_2$OCH$_3$ | Br |

TABLE 1-continued

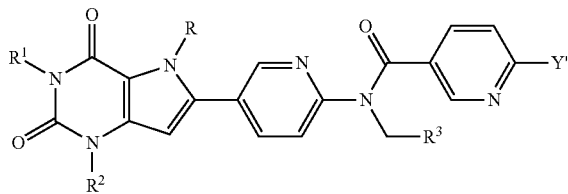

| Ex. # | R | R¹ | R² | R³ | Y' |
|---|---|---|---|---|---|
| 112. | H | i-propyl | n-propyl | CH$_3$ | Br |
| 113. | H | i-propyl | n-propyl | CH$_2$OH | Br |
| 114. | H | i-propyl | n-propyl | CH$_2$N(CH$_3$)$_2$ | Br |
| 115. | H | i-propyl | n-propyl | CH$_2$—N-piperidinyl | Br |
| 116. | H | i-propyl | n-propyl | CH$_2$—N-morpholinyl | Br |
| 117. | H | i-propyl | n-propyl | cyclopropyl | Br |
| 118. | H | i-propyl | n-propyl | CH$_2$-cyclopropyl | Br |
| 119. | H | i-propyl | n-propyl | 2-tetrahydrofuranyl | Br |
| 120. | H | i-propyl | n-propyl | CH$_2$-2-tetrahydrofuran | Br |
| 121. | H | i-propyl | n-propyl | 2-tetrahydrothienyl | Br |
| 122. | H | i-propyl | n-propyl | CH$_2$OCH$_3$ | I |
| 123. | H | i-propyl | n-propyl | CH$_3$ | I |
| 124. | H | i-propyl | n-propyl | CH$_2$OH | I |
| 125. | H | i-propyl | n-propyl | CH$_2$N(CH$_3$)$_2$ | I |
| 126. | H | i-propyl | n-propyl | CH$_2$—N-piperidinyl | I |
| 127. | H | i-propyl | n-propyl | CH$_2$—N-morpholinyl | I |
| 128. | H | i-propyl | n-propyl | cyclopropyl | I |
| 129. | H | i-propyl | n-propyl | CH$_2$-cyclopropyl | I |
| 130. | H | i-propyl | n-propyl | 2-tetrahydrofuranyl | I |
| 131. | H | i-propyl | n-propyl | CH$_2$-2-tetrahydrofuran | I |
| 132. | H | i-propyl | n-propyl | 2-tetrahydrothienyl | I |
| 133. | H | n-butyl | n-propyl | CH$_2$OCH$_3$ | H |
| 134. | H | n-butyl | n-propyl | CH$_3$ | H |
| 135. | H | n-butyl | n-propyl | CH$_2$OH | H |
| 136. | H | n-butyl | n-propyl | CH$_2$N(CH$_3$)$_2$ | H |
| 137. | H | n-butyl | n-propyl | CH$_2$—N-piperidinyl | H |
| 138. | H | n-butyl | n-propyl | CH$_2$—N-morpholinyl | H |
| 139. | H | n-butyl | n-propyl | cyclopropyl | H |
| 140. | H | n-butyl | n-propyl | CH$_2$-cyclopropyl | H |
| 141. | H | n-butyl | n-propyl | 2-tetrahydrofuranyl | H |
| 142. | H | n-butyl | n-propyl | CH$_2$-2-tetrahydrofuran | H |
| 143. | H | n-butyl | n-propyl | 2-tetrahydrothienyl | H |
| 144. | H | n-butyl | n-propyl | CH$_2$OCH$_3$ | CF$_3$ |
| 145. | H | n-butyl | n-propyl | CH$_3$ | CF$_3$ |
| 146. | H | n-butyl | n-propyl | CH$_2$OH | CF$_3$ |
| 147. | H | n-butyl | n-propyl | CH$_2$N(CH$_3$)$_2$ | CF$_3$ |
| 148. | H | n-butyl | n-propyl | CH$_2$—N-piperidinyl | CF$_3$ |
| 149. | H | n-butyl | n-propyl | CH$_2$—N-morpholinyl | CF$_3$ |
| 150. | H | n-butyl | n-propyl | cyclopropyl | CF$_3$ |
| 151. | H | n-butyl | n-propyl | CH$_2$-cyclopropyl | CF$_3$ |
| 152. | H | n-butyl | n-propyl | 2-tetrahydrofuranyl | CF$_3$ |
| 153. | H | n-butyl | n-propyl | CH$_2$-2-tetrahydrofuran | CF$_3$ |
| 154. | H | n-butyl | n-propyl | 2-tetrahydrothienyl | CF$_3$ |
| 155. | H | n-butyl | n-propyl | CH$_2$OCH$_3$ | F |
| 156. | H | n-butyl | n-propyl | CH$_3$ | F |
| 157. | H | n-butyl | n-propyl | CH$_2$OH | F |
| 158. | H | n-butyl | n-propyl | CH$_2$N(CH$_3$)$_2$ | F |
| 159. | H | n-butyl | n-propyl | CH$_2$—N-piperidinyl | F |
| 160. | H | n-butyl | n-propyl | CH$_2$—N-morpholinyl | F |
| 161. | H | n-butyl | n-propyl | cyclopropyl | F |
| 162. | H | n-butyl | n-propyl | CH$_2$-cyclopropyl | F |
| 163. | H | n-butyl | n-propyl | 2-tetrahydrofuranyl | F |
| 164. | H | n-butyl | n-propyl | CH$_2$-2-tetrahydrofuran | F |
| 165. | H | n-butyl | n-propyl | 2-tetrahydrothienyl | F |
| 166. | H | n-butyl | n-propyl | CH$_2$OCH$_3$ | Cl |
| 167. | H | n-butyl | n-propyl | CH$_3$ | Cl |
| 168. | H | n-butyl | n-propyl | CH$_2$OH | Cl |
| 169. | H | n-butyl | n-propyl | CH$_2$N(CH$_3$)$_2$ | Cl |
| 170. | H | n-butyl | n-propyl | CH$_2$—N-piperidinyl | Cl |
| 171. | H | n-butyl | n-propyl | CH$_2$—N-morpholinyl | Cl |
| 172. | H | n-butyl | n-propyl | cyclopropyl | Cl |
| 173. | H | n-butyl | n-propyl | CH$_2$-cyclopropyl | Cl |
| 174. | H | n-butyl | n-propyl | 2-tetrahydrofuranyl | Cl |
| 175. | H | n-butyl | n-propyl | CH$_2$-2-tetrahydrofuran | Cl |
| 176. | H | n-butyl | n-propyl | 2-tetrahydrothienyl | Cl |
| 177. | H | n-butyl | n-propyl | CH$_2$OCH$_3$ | Br |
| 178. | H | n-butyl | n-propyl | CH$_3$ | Br |

TABLE 1-continued

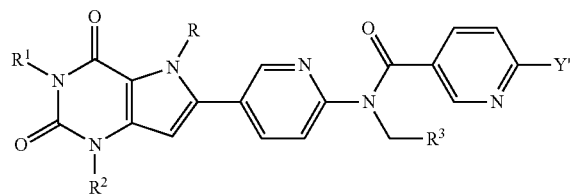 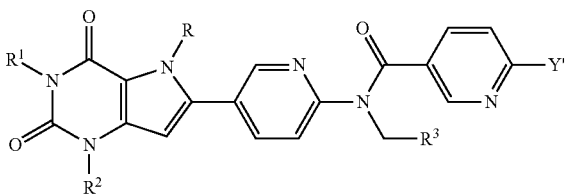

| Ex. # | R | R¹ | R² | R³ | Y' |
|---|---|---|---|---|---|
| 179. | H | n-butyl | n-propyl | CH₂OH | Br |
| 180. | H | n-butyl | n-propyl | CH₂N(CH₃)₂ | Br |
| 181. | H | n-butyl | n-propyl | CH₂—N-piperidinyl | Br |
| 182. | H | n-butyl | n-propyl | CH₂—N-morpholinyl | Br |
| 183. | H | n-butyl | n-propyl | cyclopropyl | Br |
| 184. | H | n-butyl | n-propyl | CH₂-cyclopropyl | Br |
| 185. | H | n-butyl | n-propyl | 2-tetrahydrofuranyl | Br |
| 186. | H | n-butyl | n-propyl | CH₂-2-tetrahydrofuran | Br |
| 187. | H | n-butyl | n-propyl | 2-tetrahydrothienyl | Br |
| 188. | H | n-butyl | n-propyl | CH₂OCH₃ | I |
| 189. | H | n-butyl | n-propyl | CH₃ | I |
| 190. | H | n-butyl | n-propyl | CH₂OH | I |
| 191. | H | n-butyl | n-propyl | CH₂N(CH₃)₂ | I |
| 192. | H | n-butyl | n-propyl | CH₂—N-piperidinyl | I |
| 193. | H | n-butyl | n-propyl | CH₂—N-morpholinyl | I |
| 194. | H | n-butyl | n-propyl | cyclopropyl | I |
| 195. | H | n-butyl | n-propyl | CH₂-cyclopropyl | I |
| 196. | H | n-butyl | n-propyl | 2-tetrahydrofuranyl | I |
| 197. | H | n-butyl | n-propyl | CH₂-2-tetrahydrofuran | I |
| 198. | H | n-butyl | n-propyl | 2-tetrahydrothienyl | I |
| 199. | H | i-butyl | n-propyl | CH₂OCH₃ | H |
| 200. | H | i-butyl | n-propyl | CH₃ | H |
| 201. | H | i-butyl | n-propyl | CH₂OH | H |
| 202. | H | i-butyl | n-propyl | CH₂N(CH₃)₂ | H |
| 203. | H | i-butyl | n-propyl | CH₂—N-piperidinyl | H |
| 204. | H | i-butyl | n-propyl | CH₂—N-morpholinyl | H |
| 205. | H | i-butyl | n-propyl | cyclopropyl | H |
| 206. | H | i-butyl | n-propyl | CH₂-cyclopropyl | H |
| 207. | H | i-butyl | n-propyl | 2-tetrahydrofuranyl | H |
| 208. | H | i-butyl | n-propyl | CH₂-2-tetrahydrofuran | H |
| 209. | H | i-butyl | n-propyl | 2-tetrahydrothienyl | H |
| 210. | H | i-butyl | n-propyl | CH₂OCH₃ | CF₃ |
| 211. | H | i-butyl | n-propyl | CH₃ | CF₃ |
| 212. | H | i-butyl | n-propyl | CH₂OH | CF₃ |
| 213. | H | i-butyl | n-propyl | CH₂N(CH₃)₂ | CF₃ |
| 214. | H | i-butyl | n-propyl | CH₂—N-piperidinyl | CF₃ |
| 215. | H | i-butyl | n-propyl | CH₂—N-morpholinyl | CF₃ |
| 216. | H | i-butyl | n-propyl | cyclopropyl | CF₃ |
| 217. | H | i-butyl | n-propyl | CH₂-cyclopropyl | CF₃ |
| 218. | H | i-butyl | n-propyl | 2-tetrahydrofuranyl | CF₃ |
| 219. | H | i-butyl | n-propyl | CH₂-2-tetrahydrofuran | CF₃ |
| 220. | H | i-butyl | n-propyl | 2-tetrahydrothienyl | CF₃ |
| 221. | H | i-butyl | n-propyl | CH₂OCH₃ | F |
| 222. | H | i-butyl | n-propyl | CH₃ | F |
| 223. | H | i-butyl | n-propyl | CH₂OH | F |
| 224. | H | i-butyl | n-propyl | CH₂N(CH₃)₂ | F |
| 225. | H | i-butyl | n-propyl | CH₂—N-piperidinyl | F |
| 226. | H | i-butyl | n-propyl | CH₂—N-morpholinyl | F |
| 227. | H | i-butyl | n-propyl | cyclopropyl | F |
| 228. | H | i-butyl | n-propyl | CH₂-cyclopropyl | F |
| 229. | H | i-butyl | n-propyl | 2-tetrahydrofuranyl | F |
| 230. | H | i-butyl | n-propyl | CH₂-2-tetrahydrofuran | F |
| 231. | H | i-butyl | n-propyl | 2-tetrahydrothienyl | F |
| 232. | H | i-butyl | n-propyl | CH₂OCH₃ | Cl |
| 233. | H | i-butyl | n-propyl | CH₃ | Cl |
| 234. | H | i-butyl | n-propyl | CH₂OH | Cl |
| 235. | H | i-butyl | n-propyl | CH₂N(CH₃)₂ | Cl |
| 236. | H | i-butyl | n-propyl | CH₂—N-piperidinyl | Cl |
| 237. | H | i-butyl | n-propyl | CH₂—N-morpholinyl | Cl |
| 238. | H | i-butyl | n-propyl | cyclopropyl | Cl |
| 239. | H | i-butyl | n-propyl | CH₂-cyclopropyl | Cl |
| 240. | H | i-butyl | n-propyl | 2-tetrahydrofuranyl | Cl |
| 241. | H | i-butyl | n-propyl | CH₂-2-tetrahydrofuran | Cl |
| 242. | H | i-butyl | n-propyl | 2-tetrahydrothienyl | Cl |
| 243. | H | i-butyl | n-propyl | CH₂OCH₃ | Br |
| 244. | H | i-butyl | n-propyl | CH₃ | Br |
| 245. | H | i-butyl | n-propyl | CH₂OH | Br |
| 246. | H | i-butyl | n-propyl | CH₂N(CH₃)₂ | Br |
| 247. | H | i-butyl | n-propyl | CH₂—N-piperidinyl | Br |
| 248. | H | i-butyl | n-propyl | CH₂—N-morpholinyl | Br |
| 249. | H | i-butyl | n-propyl | cyclopropyl | Br |
| 250. | H | i-butyl | n-propyl | CH₂-cyclopropyl | Br |
| 251. | H | i-butyl | n-propyl | 2-tetrahydrofuranyl | Br |
| 252. | H | i-butyl | n-propyl | CH₂-2-tetrahydrofuran | Br |
| 253. | H | i-butyl | n-propyl | 2-tetrahydrothienyl | Br |
| 254. | H | i-butyl | n-propyl | CH₂OCH₃ | I |
| 255. | H | i-butyl | n-propyl | CH₃ | I |
| 256. | H | i-butyl | n-propyl | CH₂OH | I |
| 257. | H | i-butyl | n-propyl | CH₂N(CH₃)₂ | I |
| 258. | H | i-butyl | n-propyl | CH₂—N-piperidinyl | I |
| 259. | H | i-butyl | n-propyl | CH₂—N-morpholinyl | I |
| 260. | H | i-butyl | n-propyl | cyclopropyl | I |
| 261. | H | i-butyl | n-propyl | CH₂-cyclopropyl | I |
| 262. | H | i-butyl | n-propyl | 2-tetrahydrofuranyl | I |
| 263. | H | i-butyl | n-propyl | CH₂-2-tetrahydrofuran | I |
| 264. | H | i-butyl | n-propyl | 2-tetrahydrothienyl | I |
| 265. | H | cyclobutyl | n-propyl | CH₂OCH₃ | H |
| 266. | H | cyclobutyl | n-propyl | CH₃ | H |
| 267. | H | cyclobutyl | n-propyl | CH₂OH | H |
| 268. | H | cyclobutyl | n-propyl | CH₂N(CH₃)₂ | H |
| 269. | H | cyclobutyl | n-propyl | CH₂—N-piperidinyl | H |
| 270. | H | cyclobutyl | n-propyl | CH₂—N-morpholinyl | H |
| 271. | H | cyclobutyl | n-propyl | cyclopropyl | H |
| 272. | H | cyclobutyl | n-propyl | CH₂-cyclopropyl | H |
| 273. | H | cyclobutyl | n-propyl | 2-tetrahydrofuranyl | H |
| 274. | H | cyclobutyl | n-propyl | CH₂-2-tetrahydrofuran | H |
| 275. | H | cyclobutyl | n-propyl | 2-tetrahydrothienyl | H |
| 276. | H | cyclobutyl | n-propyl | CH₂OCH₃ | CF₃ |
| 277. | H | cyclobutyl | n-propyl | CH₃ | CF₃ |
| 278. | H | cyclobutyl | n-propyl | CH₂OH | CF₃ |
| 279. | H | cyclobutyl | n-propyl | CH₂N(CH₃)₂ | CF₃ |
| 280. | H | cyclobutyl | n-propyl | CH₂—N-piperidinyl | CF₃ |
| 281. | H | cyclobutyl | n-propyl | CH₂—N-morpholinyl | CF₃ |
| 282. | H | cyclobutyl | n-propyl | cyclopropyl | CF₃ |
| 283. | H | cyclobutyl | n-propyl | CH₂-cyclopropyl | CF₃ |
| 284. | H | cyclobutyl | n-propyl | 2-tetrahydrofuranyl | CF₃ |
| 285. | H | cyclobutyl | n-propyl | CH₂-2-tetrahydrofuran | CF₃ |
| 286. | H | cyclobutyl | n-propyl | 2-tetrahydrothienyl | CF₃ |
| 287. | H | cyclobutyl | n-propyl | CH₂OCH₃ | F |
| 288. | H | cyclobutyl | n-propyl | CH₃ | F |
| 289. | H | cyclobutyl | n-propyl | CH₂OH | F |
| 290. | H | cyclobutyl | n-propyl | CH₂N(CH₃)₂ | F |
| 291. | H | cyclobutyl | n-propyl | CH₂—N-piperidinyl | F |
| 292. | H | cyclobutyl | n-propyl | CH₂—N-morpholinyl | F |
| 293. | H | cyclobutyl | n-propyl | cyclopropyl | F |
| 294. | H | cyclobutyl | n-propyl | CH₂-cyclopropyl | F |
| 295. | H | cyclobutyl | n-propyl | 2-tetrahydrofuranyl | F |
| 296. | H | cyclobutyl | n-propyl | CH₂-2-tetrahydrofuran | F |
| 297. | H | cyclobutyl | n-propyl | 2-tetrahydrothienyl | F |
| 298. | H | cyclobutyl | n-propyl | CH₂OCH₃ | Cl |
| 299. | H | cyclobutyl | n-propyl | CH₃ | Cl |
| 300. | H | cyclobutyl | n-propyl | CH₂OH | Cl |
| 301. | H | cyclobutyl | n-propyl | CH₂N(CH₃)₂ | Cl |
| 302. | H | cyclobutyl | n-propyl | CH₂—N-piperidinyl | Cl |
| 303. | H | cyclobutyl | n-propyl | CH₂—N-morpholinyl | Cl |
| 304. | H | cyclobutyl | n-propyl | cyclopropyl | Cl |
| 305. | H | cyclobutyl | n-propyl | CH₂-cyclopropyl | Cl |
| 306. | H | cyclobutyl | n-propyl | 2-tetrahydrofuranyl | Cl |
| 307. | H | cyclobutyl | n-propyl | CH₂-2-tetrahydrofuran | Cl |
| 308. | H | cyclobutyl | n-propyl | 2-tetrahydrothienyl | Cl |
| 309. | H | cyclobutyl | n-propyl | CH₂OCH₃ | Br |
| 310. | H | cyclobutyl | n-propyl | CH₃ | Br |
| 311. | H | cyclobutyl | n-propyl | CH₂OH | Br |
| 312. | H | cyclobutyl | n-propyl | CH₂N(CH₃)₂ | Br |

TABLE 1-continued

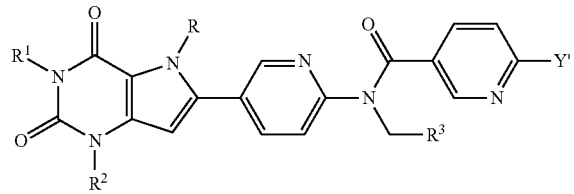

| Ex. # | R | R¹ | R² | R³ | Y' |
|---|---|---|---|---|---|
| 313. | H | cyclobutyl | n-propyl | CH₂—N-piperidinyl | Br |
| 314. | H | cyclobutyl | n-propyl | CH₂—N-morpholinyl | Br |
| 315. | H | cyclobutyl | n-propyl | cyclopropyl | Br |
| 316. | H | cyclobutyl | n-propyl | CH₂-cyclopropyl | Br |
| 317. | H | cyclobutyl | n-propyl | 2-tetrahydrofuranyl | Br |
| 318. | H | cyclobutyl | n-propyl | CH₂-2-tetrahydrofuran | Br |
| 319. | H | cyclobutyl | n-propyl | 2-tetrahydrothienyl | Br |
| 320. | H | cyclobutyl | n-propyl | CH₂OCH₃ | I |
| 321. | H | cyclobutyl | n-propyl | CH₃ | I |
| 322. | H | cyclobutyl | n-propyl | CH₂OH | I |
| 323. | H | cyclobutyl | n-propyl | CH₂N(CH₃)₂ | I |
| 324. | H | cyclobutyl | n-propyl | CH₂—N-piperidinyl | I |
| 325. | H | cyclobutyl | n-propyl | CH₂—N-morpholinyl | I |
| 326. | H | cyclobutyl | n-propyl | cyclopropyl | I |
| 327. | H | cyclobutyl | n-propyl | CH₂-cyclopropyl | I |
| 328. | H | cyclobutyl | n-propyl | 2-tetrahydrofuranyl | I |
| 329. | H | cyclobutyl | n-propyl | CH₂-2-tetrahydrofuran | I |
| 330. | H | cyclobutyl | n-propyl | 2-tetrahydrothienyl | I |
| 331. | H | cyclopropyl-methyl- | n-propyl | CH₂OCH₃ | H |
| 332. | H | cyclopropyl-methyl- | n-propyl | CH₃ | H |
| 333. | H | cyclopropyl-methyl- | n-propyl | CH₂OH | H |
| 334. | H | cyclopropyl-methyl- | n-propyl | CH₂N(CH₃)₂ | H |
| 335. | H | cyclopropyl-methyl- | n-propyl | CH₂—N-piperidinyl | H |
| 336. | H | cyclopropyl-methyl- | n-propyl | CH₂—N-morpholinyl | H |
| 337. | H | cyclopropyl-methyl- | n-propyl | cyclopropyl | H |
| 338. | H | cyclopropyl-methyl- | n-propyl | CH₂-cyclopropyl | H |
| 339. | H | cyclopropyl-methyl- | n-propyl | 2-tetrahydrofuranyl | H |
| 340. | H | cyclopropyl-methyl- | n-propyl | CH₂-2-tetrahydrofuran | H |
| 341. | H | cyclopropyl-methyl- | n-propyl | 2-tetrahydrothienyl | H |
| 342. | H | cyclopropyl-methyl- | n-propyl | CH₂OCH₃ | CF₃ |
| 343. | H | cyclopropyl-methyl- | n-propyl | CH₃ | CF₃ |
| 344. | H | cyclopropyl-methyl- | n-propyl | CH₂OH | CF₃ |
| 345. | H | cyclopropyl-methyl- | n-propyl | CH₂N(CH₃)₂ | CF₃ |
| 346. | H | cyclopropyl-methyl- | n-propyl | CH₂—N-piperidinyl | CF₃ |
| 347. | H | cyclopropyl-methyl- | n-propyl | CH₂—N-morpholinyl | CF₃ |
| 348. | H | cyclopropyl-methyl- | n-propyl | cyclopropyl | CF₃ |
| 349. | H | cyclopropyl-methyl- | n-propyl | CH₂-cyclopropyl | CF₃ |
| 350. | H | cyclopropyl-methyl- | n-propyl | 2-tetrahydrofuranyl | CF₃ |
| 351. | H | cyclopropyl-methyl- | n-propyl | CH₂-2-tetrahydrofuran | CF₃ |
| 352. | H | cyclopropyl-methyl- | n-propyl | 2-tetrahydrothienyl | CF₃ |
| 353. | H | cyclopropyl-methyl- | n-propyl | CH₂OCH₃ | F |
| 354. | H | cyclopropyl-methyl- | n-propyl | CH₃ | F |

TABLE 1-continued

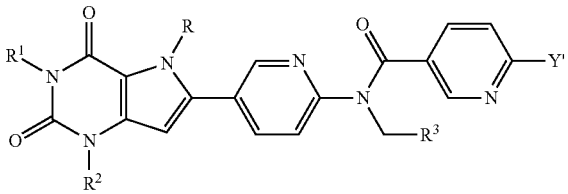

| Ex. # | R | R¹ | R² | R³ | Y' |
|---|---|---|---|---|---|
| 355. | H | cyclopropyl-methyl- | n-propyl | CH₂OH | F |
| 356. | H | cyclopropyl-methyl- | n-propyl | CH₂N(CH₃)₂ | F |
| 357. | H | cyclopropyl-methyl- | n-propyl | CH₂—N-piperidinyl | F |
| 358. | H | cyclopropyl-methyl- | n-propyl | CH₂—N-morpholinyl | F |
| 359. | H | cyclopropyl-methyl- | n-propyl | cyclopropyl | F |
| 360. | H | cyclopropyl-methyl- | n-propyl | CH₂-cyclopropyl | F |
| 361. | H | cyclopropyl-methyl- | n-propyl | 2-tetrahydrofuranyl | F |
| 362. | H | cyclopropyl-methyl- | n-propyl | CH₂-2-tetrahydrofuran | F |
| 363. | H | cyclopropyl-methyl- | n-propyl | 2-tetrahydrothienyl | F |
| 364. | H | cyclopropyl-methyl- | n-propyl | CH₂OCH₃ | Cl |
| 365. | H | cyclopropyl-methyl- | n-propyl | CH₃ | Cl |
| 366. | H | cyclopropyl-methyl- | n-propyl | CH₂OH | Cl |
| 367. | H | cyclopropyl-methyl- | n-propyl | CH₂N(CH₃)₂ | Cl |
| 368. | H | cyclopropyl-methyl- | n-propyl | CH₂—N-piperidinyl | Cl |
| 369. | H | cyclopropyl-methyl- | n-propyl | CH₂—N-morpholinyl | Cl |
| 370. | H | cyclopropyl-methyl- | n-propyl | cyclopropyl | Cl |
| 371. | H | cyclopropyl-methyl- | n-propyl | CH₂-cyclopropyl | Cl |
| 372. | H | cyclopropyl-methyl- | n-propyl | 2-tetrahydrofuranyl | Cl |
| 373. | H | cyclopropyl-methyl- | n-propyl | CH₂-2-tetrahydrofuran | Cl |
| 374. | H | cyclopropyl-methyl- | n-propyl | 2-tetrahydrothienyl | Cl |
| 375. | H | cyclopropyl-methyl- | n-propyl | CH₂OCH₃ | Br |
| 376. | H | cyclopropyl-methyl- | n-propyl | CH₃ | Br |
| 377. | H | cyclopropyl-methyl- | n-propyl | CH₂OH | Br |
| 378. | H | cyclopropyl-methyl- | n-propyl | CH₂N(CH₃)₂ | Br |
| 379. | H | cyclopropyl-methyl- | n-propyl | CH₂—N-piperidinyl | Br |
| 380. | H | cyclopropyl-methyl- | n-propyl | CH₂—N-morpholinyl | Br |
| 381. | H | cyclopropyl-methyl- | n-propyl | cyclopropyl | Br |
| 382. | H | cyclopropyl-methyl- | n-propyl | CH₂-cyclopropyl | Br |
| 383. | H | cyclopropyl-methyl- | n-propyl | 2-tetrahydrofuranyl | Br |
| 384. | H | cyclopropyl-methyl- | n-propyl | CH₂-2-tetrahydrofuran | Br |
| 385. | H | cyclopropyl-methyl- | n-propyl | 2-tetrahydrothienyl | Br |
| 386. | H | cyclopropyl-methyl- | n-propyl | CH₂OCH₃ | I |
| 387. | H | cyclopropyl-methyl- | n-propyl | CH₃ | I |

TABLE 1-continued

| Ex. # | R | $R^1$ | $R^2$ | $R^3$ | Y' |
|---|---|---|---|---|---|
| 388. | H | cyclopropyl-methyl- | n-propyl | $CH_2OH$ | I |
| 389. | H | cyclopropyl-methyl- | n-propyl | $CH_2N(CH_3)_2$ | I |
| 390. | H | cyclopropyl-methyl- | n-propyl | $CH_2$—N-piperidinyl | I |
| 391. | H | cyclopropyl-methyl- | n-propyl | $CH_2$—N-morpholinyl | I |
| 392. | H | cyclopropyl-methyl- | n-propyl | cyclopropyl | I |
| 393. | H | cyclopropyl-methyl- | n-propyl | $CH_2$-cyclopropyl | I |
| 394. | H | cyclopropyl-methyl- | n-propyl | 2-tetrahydrofuranyl | I |
| 395. | H | cyclopropyl-methyl- | n-propyl | $CH_2$-2-tetrahydrofuran | I |
| 396. | H | cyclopropyl-methyl- | n-propyl | 2-tetrahydrothienyl | I |

TABLE 2

Examples 1-396 of Table 2 correspond to Examples 1-396 of Table 1.

Numerous modifications and variations of the present invention are possible in light of the above teachings. It is therefore to be understood that within the scope of the appended claims, the invention may be practiced otherwise that as specifically described herein.

What is claimed is:

1. A method for inhibiting, relieving and/or ameliorating asthma, allergies by $A_{2B}$ antagonism, sinusitis or allergic rhinitis in a mammal comprising administering to the mammal an effective amount of a compound of formula I or a stereoisomer or a pharmaceutically acceptable salt thereof:

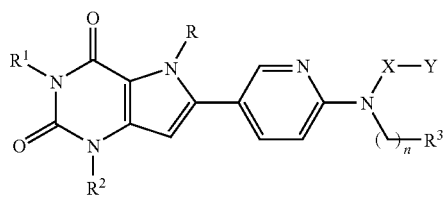

I wherein:
R is selected from: H, OH, $C_{1-6}$ alkyl, halo-$C_{1-8}$ alkyl, $C_{3-6}$ alkenyl, $C_{3-6}$ alkynyl, $(C_{3-8}$ cycloalkyl)$C_{1-8}$ alkylene, $(C_{4-10}$ heterocycle)$C_{1-8}$ alkylene, $(C_{6-10}$ aryl)$C_{1-8}$ alkylene, and $(C_{5-10}$ heteroaryl)$C_{1-8}$ alkylene, wherein R optionally is substituted with 1 $R^d$;

$R^d$ is independently selected from: F, Cl, Br, I, $C_{1-6}$ alkyl, $C_{2-6}$ alkenyl, $C_{2-6}$ alkynyl, $OC_{1-6}$ alkyl, $NO_2$, —CN, $CF_3$, and $OCF_3$;

$R^1$ and $R^2$ are independently selected from: H, $C_{1-8}$ alkyl, $C_{3-8}$ alkenyl, $C_{3-8}$ alkynyl, $C_{1-8}$ alkoxy, $C_{3-8}$ cycloalkyl, $(C_{3-8}$ cycloalkyl)$C_{1-4}$ alkylene, $C_{4-10}$ heterocycle, $(C_{4-10}$ heterocycle)$C_{1-8}$ alkylene, $C_{6-10}$ aryl, $(C_{6-10}$ aryl)$C_{1-8}$ alkylene, $C_{5-10}$ heteroaryl, and $(C_{5-10}$ heteroaryl)$C_{1-8}$ alkylene, wherein $R^1$ and $R^2$ are independently optionally substituted with 1-2 $R^{1a}$;

$R^{1a}$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_a NO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

$R^a$ is independently selected from: H, $C_{1-6}$ alkyl, $C_{2-6}$ alkenyl, $C_{2-6}$ alkynyl, $C_{3-8}$ cycloalkyl, $(C_{3-8}$ cycloalkyl)$C_{1-8}$ alkylene, $C_{4-10}$ heterocycle, $(C_{4-10}$ heterocycle)$C_{1-8}$ alkylene, $C_{6-10}$ aryl, $(C_{6-10}$ aryl)$C_{1-8}$ alkylene, $C_{5-10}$ heteroaryl, and $(C_{5-10}$ heteroaryl)$C_{1-8}$ alkylene, wherein the alkyl is optionally interrupted with 1-2 heteroatoms selected from the group consisting of —O—, —$S(O)_p$— and —$NR^b$—;

$R^b$ is independently selected from the group consisting of H, $C_{1-6}$ alkyl, and benzyl;

$R^3$ is selected from: OH, $C_{1-8}$ alkoxy, $NR^{3a}R^{3b}$, $C_{3-8}$ cycloalkyl, $C_{4-10}$ heterocycle, $C_{6-10}$ aryl, and $C_{5-10}$ heteroaryl, wherein the cycloalkyl, heterocycle, aryl, and heteroaryl are optionally substituted with 1-2 $R^{3c}$;

$R^{3a}$ and $R^{3b}$ are independently selected from: $C_{1-8}$ alkyl, $C_{2-8}$ alkenyl, $C_{2-8}$ alkynyl, phenyl, and benzyl;

$R^{3c}$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

X is selected from: $(CH_2)_q$, $(CH_2)_rC(O)$, and $(CH_2)_rC(O)NR^4$;

$R^4$ is selected from: H, $C_{1-4}$ alkyl, $C_{1-4}$ alkoxy, and $C_{1-4}$ haloalkyl;

Y is selected from: 5-10 membered heteroaryl and 6-10 membered aryl, wherein Y is optionally substituted with 1-4 $Y^1$;

$Y^1$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

a is independently selected from the group consisting of 0, 1, and 2;

n is independently selected from: 1, 2, and 3;

p is independently selected from: 0, 1, and 2;

q is independently selected from 1, 2, 3, and 4; and, r is independently selected from 0, 1, 2, and 3.

2. The method according to claim 1, wherein the compound is of formula II or a stereoisomer or a pharmaceutically acceptable salt thereof:

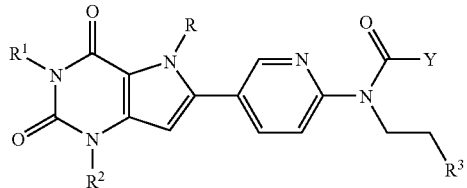

II wherein:

R is selected from: H and $C_{1-4}$ alkyl;

$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl)$C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;

$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle are optionally substituted with 1-2 $R^{3c}$;

$R^{3a}$ and $R^{3b}$ are independently selected from: $C_{1-4}$ alkyl, phenyl, and benzyl;

$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

Y is selected from: 5-6 membered heteroaryl and phenyl, wherein Y is optionally substituted with 1-2 $Y^1$;

$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and, $R^a$ is independently selected from: H, $C_{1-4}$ alkyl, $C_{3-6}$ cycloalkyl, phenyl, and benzyl.

3. The method according to claim 2, wherein:

R is H;

$R^1$ and $R^2$ are independently selected from: n-propyl, cyclopropylmethyl, and cyclobutyl;

$R^3$ is selected from: cyclopropyl, cyclobutyl, N-pyrrolidino, N-piperidino, N-piperazino, and N-morpholino;

Y is selected from: pyridyl and pyrimidyl, wherein Y is optionally substituted with 1-2 $Y^1$; and, $Y^1$ is independently selected from: F, Cl, $CH_3$, $OCH_3$, $NO_2$, —CN, and $CF_3$.

4. The method according to claim 3, wherein:

$R^1$ is selected from: n-propyl and cyclopropylmethyl; and, $R^2$ is n-propyl.

5. The method according to claim 3, wherein:

$R^1$ is n-propyl; and, $R^2$ is n-propyl.

6. The method according to claim 1, wherein the compound is of formula IV or a stereoisomer or a pharmaceutically acceptable salt thereof:

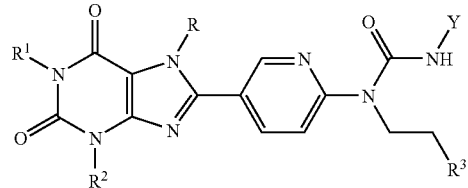

IV wherein:

R is selected from: H and $C_{1-4}$ alkyl;

$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl)$C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;

$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle are optionally substituted with 1-2 $R^{3c}$;

$R^{3a}$ and $R^{3b}$ are independently selected from: $C_{1-4}$ alkyl, phenyl, and benzyl;

$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

Y is selected from: 5-6 membered heteroaryl and phenyl, wherein Y is optionally substituted with 1-2 $Y^1$;

$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and, $R^a$ is independently selected from: H, $C_{1-4}$ alkyl, $C_{3-6}$ cycloalkyl, phenyl, and benzyl.

7. The method according to claim 1, wherein the compound is of formula V or VI or stereoisomer or a pharmaceutically acceptable salt thereof:

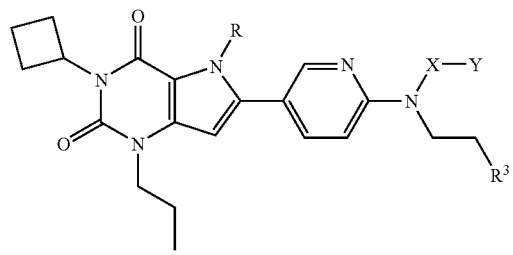

V

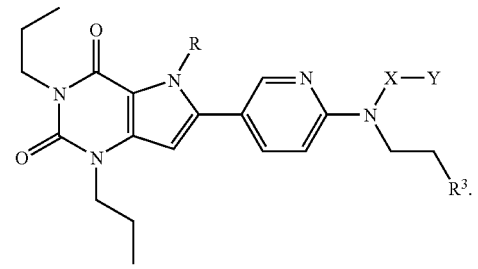

VI

8. The method according to claim 1, wherein the compound is:

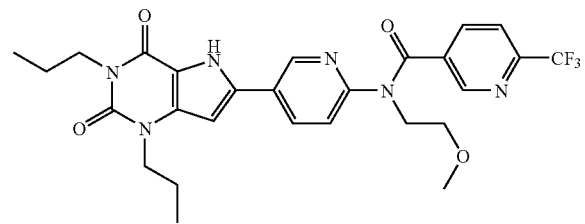 [SMILES: CCCn1c(=O)c2[nH]c(-c3ccc(N(CCOC)C(=O)c4ccc(C(F)(F)F)nc4)nc3)cc2n(CCC)c1=O]

or a pharmaceutically acceptable salt thereof.

9. The method according to claim 1, wherein the compound is selected from

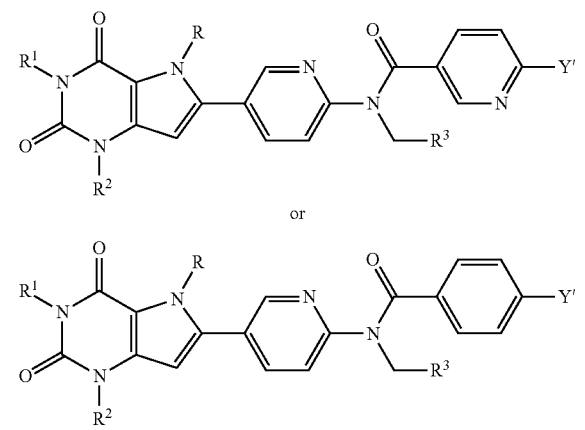

wherein R, $R^2$, $R^3$ and Y' are as defined in the following table:

| Ex.# | R | $R^1$ | $R^2$ | $R^3$ | Y' |
|---|---|---|---|---|---|
| 1 | H | n-propyl | n-propyl | $CH_2OCH_3$ | H |
| 2 | H | n-propyl | n-propyl | $CH_3$ | H |
| 3 | H | n-propyl | n-propyl | $CH_2OH$ | H |
| 4 | H | n-propyl | n-propyl | $CH_2N(CH_3)_2$ | H |
| 5 | H | p-propyl | n-propyl | $CH_2$-N-piperdinyl | H |
| 6 | H | n-propyl | n-propyl | $CH_2$-N-morpholinyl | FI |
| 7 | H | n-propyl | n-propyl | cyclopropyl | H |
| 8 | H | n-propyl | n-propyl | $CH_2$cyclopropyl | H |
| 9 | H | n-propyl | n-propyl | 2-tetrahydrofuranyl | H |
| 10 | H | n-propyl | n-propyl | $CH_2$-2-tetrahydrofuran | H |
| 11 | H | n-propyl | n-propyl | 2-tetrahydrothienyl | H |
| 12 | H | n-propyl | n-propyl | $CH_2OCH_3$ | $CF_3$ |
| 13 | H | n-propyl | n-propyl | $CH_3$ | $CF_3$ |
| 14 | H | n-propyl | n-propyl | $CH_2OH$ | $CF_3$ |
| 15 | H | n-propyl | n-propyl | $CH_2N(CH_3)_2$ | $CF_3$ |
| 16 | H | n-propyl | n-propyl | $CH_2$-N-piperdinyl | $CF_3$ |
| 17 | H | n-propyl | n-propyl | $CH_2$-N-morpholinyl | $CF_3$ |
| 18 | H | n-propyl | n-propyl | cyclopropyl | $CF_3$ |
| 19 | H | n-propyl | n-propyl | $CH_2$-cyclopropyl | $CF_3$ |
| 20 | H | n-propyl | n-propyl | 2-tetrahydrofuranyl | $CF_3$ |
| 21 | H | n-propyl | n-propyl | $CH_2$-2-tetrahydrofuran | $CF_3$ |
| 22 | H | n-propyl | n-propyl | 2-tetrahydrothienyl | $CF_3$ |
| 23 | H | n-propyl | n-propyl | $CH_2OCH_3$ | F |
| 24 | H | n-propyl | n-propyl | $CH_3$ | F |
| 25 | H | n-propyl | n-propyl | $CH_2OH$ | F |
| 26 | H | n-propyl | n-propyl | $CH_2N(CH_3)_2$ | F |
| 27 | H | n-propyl | n-propyl | $CH_2$-N-piperdinyl | F |
| 28 | H | n-propyl | n-propyl | $CH_2$-N-morpholinyl | F |
| 29 | H | n-propyl | n-propyl | cyclopropyl | F |
| 30 | H | n-propyl | n-propyl | $CH_2$-cyclopropyl | F |
| 31 | H | n-propyl | n-propyl | 2-tetrahydrofuranyl | F |
| 32 | H | n-propyl | n-propyl | $CH_2$-2-tetrahydrofuran | F |
| 33 | H | n-propyl | n-propyl | 2-tetrahydrothienyl | F |
| 34 | H | n-propyl | n-propyl | $CH_2OCH_3$ | Cl |
| 35 | H | n-propyl | n-propyl | $CH_3$ | Cl |
| 36 | H | n-propyl | n-propyl | $CH_2OH$ | Cl |
| 37 | H | n-propyl | n-propyl | $CH_2N(CH_3)_2$ | Cl |
| 38 | H | n-propyl | n-propyl | $CH_2$-N-piperdinyl | Cl |
| 39 | H | n-propyl | n-propyl | $CH_2$-N-morpholinyl | Cl |
| 40 | H | n-propyl | n-propyl | cyclopropyl | Cl |
| 41 | H | n-propyl | n-propyl | $CH_2$-cyclopropyl | Cl |
| 42 | H | n-propyl | n-propyl | 2-tetrahydrofuranyl | Cl |
| 43 | H | n-propyl | n-propyl | $CH_2$-2-tetrahydrofuran | Cl |
| 44 | H | n-propyl | n-propyl | 2-tetrahydrothienyl | Cl |
| 45 | H | n-propyl | n-propyl | $CH_2OCH_3$ | Br |
| 46 | H | n-propyl | n-propyl | $CH_3$ | Br |
| 47 | H | n-propyl | n-propyl | $CH_2OH$ | Br |
| 48 | H | n-propyl | n-propyl | $CH_2N(CH_3)_2$ | Br |
| 49 | H | n-propyl | n-propyl | $CH_2$-N-piperdinyl | Br |
| 50 | H | n-propyl | n-propyl | $CH_2$-N-morpholinyl | Br |
| 51 | H | n-propyl | n-propyl | cyclopropyl | Br |
| 52 | H | n-propyl | n-propyl | $CH_2$-cyclopropyl | Br |
| 53 | H | n-propyl | n-propyl | 2-tetrahydrofuranyl | Br |
| 54 | H | n-propyl | n-propyl | $CH_2$-2-tetrahydrofuran | Br |
| 55 | H | n-propyl | n-propyl | 2-tetrahydrothienyl | Br |
| 56 | H | n-propyl | n-propyl | $CH_2OCH_3$ | I |
| 57 | H | n-propyl | n-propyl | $CH_3$ | I |
| 58 | H | n-propyl | n-propyl | $CH_2OH$ | I |
| 59 | H | n-propyl | n-propyl | $CH_2N(CH_3)_2$ | I |
| 60 | H | n-propyl | n-propyl | $CH_2$-N-piperdinyl | I |
| 61 | H | n-propyl | n-propyl | $CH_2$-N-morpholinyl | I |
| 62 | H | n-propyl | n-propyl | cyclopropyl | I |
| 63 | H | n-propyl | n-propyl | $CH_2$-cyclopropyl | I |
| 64 | H | n-propyl | n-propyl | 2-tetrahydrofuranyl | I |
| 65 | H | n-propyl | n-propyl | $CH_2$-2-tetrahydrofuran | I |
| 66 | H | n-propyl | n-propyl | 2-tetrahydrothienyl | I |
| 67 | H | i-propyl | n-propyl | $CH_2OCH_3$ | H |
| 68 | H | i-propyl | n-propyl | $CH_3$ | H |
| 69 | H | i-propyl | n-propyl | $CH_2OH$ | H |
| 70 | H | i-propyl | n-propyl | $CH_2N(CH_3)_2$ | H |
| 71 | H | i-propyl | n-propyl | $CH_2$-N-piperdinyl | H |
| 72 | H | i-propyl | n-propyl | $CH_2$-N-morpholinyl | H |
| 73 | H | i-propyl | n-propyl | cyclopropyl | H |
| 74 | H | i-propyl | n-propyl | $CH_2$-cyclopropyl | H |
| 75 | H | i-propyl | n-propyl | 2-tetrahydrofuranyl | H |
| 76 | H | i-propyl | n-propyl | $CH_2$-2-tetrahydrofuran | H |
| 77 | H | i-propyl | n-propyl | 2-tetrahydrothienyl | H |
| 78 | H | i-propyl | n-propyl | $CH_2OCH_3$ | $CF_3$ |
| 79 | H | i-propyl | n-propyl | $CH_3$ | $CF_3$ |
| 80 | H | i-propyl | n-propyl | $CH_2OH$ | $CF_3$ |
| 81 | H | i-propyl | n-propyl | $CH_2N(CH_3)_2$ | $CF_3$ |
| 82 | H | i-propyl | n-propyl | $CH_2$-N-piperdinyl | $CF_3$ |
| 83 | H | i-propyl | n-propyl | $CH_2$-N-morpholinyl | $CF_3$ |
| 84 | H | i-propyl | n-propyl | cyclopropyl | $CF_3$ |
| 85 | H | i-propyl | n-propyl | $CH_2$-cyclopropyl | $CF_3$ |
| 86 | H | i-propyl | n-propyl | 2-tetrahydrofuranyl | $CF_3$ |
| 87 | H | i-propyl | n-propyl | $CH_2$-2-tetrahydrofuran | $CF_3$ |
| 88 | H | i-propyl | n-propyl | 2-tetrahydrothienyl | $CF_3$ |
| 89 | H | i-propyl | n-propyl | $CH_2OCH_3$ | F |
| 90 | H | i-propyl | n-propyl | $CH_3$ | F |
| 91 | H | i-propyl | n-propyl | $CH_2OH$ | F |
| 92 | H | i-propyl | n-propyl | $CH_2N(CH_3)_2$ | F |
| 93 | H | i-propyl | n-propyl | $CH_2$-N-piperdinyl | F |
| 94 | H | i-propyl | n-propyl | $CH_2$-N-morpholinyl | F |
| 95 | H | i-propyl | n-propyl | cyclopropyl | F |
| 96 | H | i-propyl | n-propyl | $CH_2$-cyclopropyl | F |
| 97 | H | i-propyl | n-propyl | 2-tetrahydrofuranyl | F |
| 98 | H | i-propyl | n-propyl | $CH_2$-2-tetrahydrofuran | F |
| 99 | H | i-propyl | n-propyl | 2-tetrahydrothienyl | F |
| 100 | H | i-propyl | n-propyl | $CH_2OCH_3$ | Cl |
| 101 | H | i-propyl | n-propyl | $CH_3$ | Cl |
| 102 | H | i-propyl | n-propyl | $CH_2OH$ | Cl |
| 103 | H | i-propyl | n-propyl | $CH_2N(CH_3)_2$ | Cl |
| 104 | H | i-propyl | n-propyl | $CH_2$-N-piperdinyl | Cl |
| 105 | H | i-propyl | n-propyl | $CH_2$-N-morpholinyl | Cl |
| 106 | H | i-propyl | n-propyl | cyclopropyl | Cl |
| 107 | H | i-propyl | n-propyl | $CH_2$-cyclopropyl | Cl |

-continued

| Ex.# | R | R¹ | R² | R³ | Y' |
|---|---|---|---|---|---|
| 108 | H | i-propyl | n-propyl | 2-tetrahydrofuranyl | Cl |
| 109 | H | i-propyl | n-propyl | CH₂-2-tetrahydrofuran | Cl |
| 110 | H | i-propyl | n-propyl | 2-tetrahydrothienyl | Cl |
| 111 | H | i-propyl | n-propyl | CH₂OCH₃ | Br |
| 112 | H | i-propyl | n-propyl | CH₃ | Br |
| 113 | H | i-propyl | n-propyl | CH₂OH | Br |
| 114 | H | i-propyl | n-propyl | CH₂N(CH₃)₂ | Br |
| 115 | H | i-propyl | n-propyl | CH₂-N-piperdinyl | Br |
| 116 | H | i-propyl | n-propyl | CH₂-N-morpholinyl | Br |
| 117 | H | i-propyl | n-propyl | cyclopropyl | Br |
| 118 | H | i-propyl | n-propyl | CH₂-cyclopropyl | Br |
| 119 | H | i-propyl | n-propyl | 2-tetrahydrofuranyl | Br |
| 120 | H | i-propyl | n-propyl | CH₂-2-tetrahydrofuran | Br |
| 121 | H | i-propyl | n-propyl | 2-tetrahydrothienyl | Br |
| 122 | H | i-propyl | n-propyl | CH₂OCH₃ | I |
| 123 | H | i-propyl | n-propyl | CH₃ | I |
| 124 | H | i-propyl | n-propyl | CH₂OH | I |
| 125 | H | i-propyl | n-propyl | CH₂N(CH₃)₂ | I |
| 126 | H | i-propyl | n-propyl | CH₂-N-piperdinyl | I |
| 127 | H | i-propyl | n-propyl | CH₂-N-morpholinyl | I |
| 128 | H | i-propyl | n-propyl | cyclopropyl | I |
| 129 | H | i-propyl | n-propyl | CH₂-cyclopropyl | I |
| 130 | H | i-propyl | n-propyl | 2-tetrahydrofuranyl | I |
| 131 | H | i-propyl | n-propyl | CH₂-2-tetrahydrofuran | I |
| 132 | H | i-propyl | n-propyl | 2-tetrahydrothienyl | I |
| 133 | H | n-butyl | n-propyl | CH₂OCH₃ | H |
| 134 | H | n-butyl | n-propyl | CH₃ | H |
| 135 | H | n-butyl | n-propyl | CH₂OH | H |
| 136 | H | n-butyl | n-propyl | CH₂N(CH₃)₂ | H |
| 137 | H | n-butyl | n-propyl | CH₂-N-piperdinyl | H |
| 138 | H | n-butyl | n-propyl | CH₂-N-morpholinyl | H |
| 139 | H | n-butyl | n-propyl | cyclopropyl | H |
| 140 | H | n-butyl | n-propyl | CH₂-cyclopropyl | H |
| 141 | H | n-butyl | n-propyl | 2-tetrahydrofuranyl | H |
| 142 | H | n-butyl | n-propyl | CH₂-2-tetrahydrofuran | H |
| 143 | H | n-butyl | n-propyl | 2-tetrahydrothienyl | H |
| 144 | H | n-butyl | n-propyl | CH₂OCH₃ | CF₃ |
| 145 | H | n-butyl | n-propyl | CH₃ | CF₃ |
| 146 | H | n-butyl | n-propyl | CH₂OH | CF₃ |
| 147 | H | n-butyl | n-propyl | CH₂N(CH₃)₂ | CF₃ |
| 148 | H | n-butyl | n-propyl | CH₂-N-piperdinyl | CF₃ |
| 149 | H | n-butyl | n-propyl | CH₂-N-morpholinyl | CF₃ |
| 150 | H | n-butyl | n-propyl | cyclopropyl | CF₃ |
| 151 | H | n-butyl | n-propyl | CH₂-cyclopropyl | CF₃ |
| 152 | H | n-butyl | n-propyl | 2-tetrahydrofuranyl | CF₃ |
| 153 | H | n-butyl | n-propyl | CH₂-2-tetrahydrofuran | CF₃ |
| 154 | H | n-butyl | n-propyl | 2-tetrahydrothienyl | CF₃ |
| 155 | H | n-butyl | n-propyl | CH₂OCH₃ | F |
| 156 | H | n-butyl | n-propyl | CH₃ | F |
| 157 | H | n-butyl | n-propyl | CH₂OH | F |
| 158 | H | n-butyl | n-propyl | CH₂N(CH₃)₂ | F |
| 159 | H | n-butyl | n-propyl | CH₂-N-piperdinyl | F |
| 160 | H | n-butyl | n-propyl | CH₂-N-morpholinyl | F |
| 161 | H | n-butyl | n-propyl | cyclopropyl | F |
| 162 | H | n-butyl | n-propyl | CH₂-cyclopropyl | F |
| 163 | H | n-butyl | n-propyl | 2-tetrahydrofuranyl | F |
| 164 | H | n-butyl | n-propyl | CH₂-2-tetrahydrofuran | F |
| 165 | H | n-butyl | n-propyl | 2-tetrahydrothienyl | F |
| 166 | H | n-butyl | n-propyl | CH₂OCH₃ | Cl |
| 167 | H | n-butyl | n-propyl | CH₃ | Cl |
| 168 | H | n-butyl | n-propyl | CH₂OH | Cl |
| 169 | H | n-butyl | n-propyl | CH₂N(CH₃)₂ | Cl |
| 170 | H | n-butyl | n-propyl | CH₂-N-piperdinyl | Cl |
| 171 | H | n-butyl | n-propyl | CH₂-N-morpholinyl | Cl |
| 172 | H | n-butyl | n-propyl | cyclopropyl | Cl |
| 173 | H | n-butyl | n-propyl | CH₂-cyclopropyl | Cl |
| 174 | H | n-butyl | n-propyl | 2-tetrahydrofuranyl | Cl |
| 175 | H | n-butyl | n-propyl | CH₂-2-tetrahydrofuran | Cl |
| 176 | H | n-butyl | n-propyl | 2-tetrahydrothienyl | Cl |
| 177 | H | n-butyl | n-propyl | CH₂OCH₃ | Br |
| 178 | H | n-butyl | n-propyl | CH₃ | Br |
| 179 | H | n-butyl | n-propyl | CH₂OH | Br |
| 180 | H | n-butyl | n-propyl | CH₂N(CH₃)₂ | Br |
| 181 | H | n-butyl | n-propyl | CH₂-N-piperdinyl | Br |
| 182 | H | n-butyl | n-propyl | CH₂-N-morpholinyl | Br |
| 183 | H | n-butyl | n-propyl | cyclopropyl | Br |
| 184 | H | n-butyl | n-propyl | CH₂-cyclopropyl | Br |
| 185 | H | n-butyl | n-propyl | 2-tetrahydrofuranyl | Br |
| 186 | H | n-butyl | n-propyl | CH₂-2-tetrahydrofuran | Br |
| 187 | H | n-butyl | n-propyl | 2-tetrahydrothienyl | Br |
| 188 | H | n-butyl | n-propyl | CH₂OCH₃ | I |
| 189 | H | n-butyl | n-propyl | CH₃ | I |
| 190 | H | n-butyl | n-propyl | CH₂OH | I |
| 191 | H | n-butyl | n-propyl | CH₂N(CH₃)₂ | I |
| 192 | H | n-butyl | n-propyl | CH₂-N-piperdinyl | I |
| 193 | H | n-butyl | n-propyl | CH₂-N-morpholinyl | I |
| 194 | H | n-butyl | n-propyl | cyclopropyl | I |
| 195 | H | n-butyl | n-propyl | CH₂-cyclopropyl | I |
| 196 | H | n-butyl | n-propyl | 2-tetrahydrofuranyl | I |
| 197 | H | n-butyl | n-propyl | CH₂-2-tetrahydrofuran | I |
| 198 | H | n-butyl | n-propyl | 2-tetrahydrothienyl | I |
| 199 | H | i-butyl | n-propyl | CH₂OCH₃ | H |
| 200 | H | i-butyl | n-propyl | CH₃ | H |
| 201 | H | i-butyl | n-propyl | CH₂OH | H |
| 202 | H | i-butyl | n-propyl | CH₂N(CH₃)₂ | H |
| 203 | H | i-butyl | n-propyl | CH₂-N-piperdinyl | H |
| 204 | H | i-butyl | n-propyl | CH₂-N-morpholinyl | H |
| 205 | H | i-butyl | n-propyl | cyclopropyl | H |
| 206 | H | i-butyl | n-propyl | CH₂-cyclopropyl | H |
| 207 | H | i-butyl | n-propyl | 2-tetrahydrofuranyl | H |
| 208 | H | i-butyl | n-propyl | CH₂-2-tetrahydrofuran | H |
| 209 | H | i-butyl | n-propyl | 2-tetrahydrothienyl | H |
| 210 | H | i-butyl | n-propyl | CH₂OCH₃ | CF₃ |
| 211 | H | i-butyl | n-propyl | CH₃ | CF₃ |
| 212 | H | i-butyl | n-propyl | CH₂OH | CF₃ |
| 213 | H | i-butyl | n-propyl | CH₂N(CH₃)₂ | CF₃ |
| 214 | H | i-butyl | n-propyl | CH₂-N-piperdinyl | CF₃ |
| 215 | H | i-butyl | n-propyl | CH₂-N-morpholinyl | CF₃ |
| 216 | H | i-butyl | n-propyl | cyclopropyl | CF₃ |
| 217 | H | i-butyl | n-propyl | CH₂-cyclopropyl | CF₃ |
| 218 | H | i-butyl | n-propyl | 2-tetrahydrofuranyl | CF₃ |
| 219 | H | i-butyl | n-propyl | CH₂-2-tetrahydrofuran | CF₃ |
| 220 | H | i-butyl | n-propyl | 2-tetrahydrothienyl | CF₃ |
| 221 | H | i-butyl | n-propyl | CH₂OCH₃ | F |
| 222 | H | i-butyl | n-propyl | CH₃ | F |
| 223 | H | i-butyl | n-propyl | CH₂OH | F |
| 224 | H | i-butyl | n-propyl | CH₂N(CH₃)₂ | F |
| 225 | H | i-butyl | n-propyl | CH₂-N-piperdinyl | F |
| 226 | H | i-butyl | n-propyl | CH₂-N-morpholinyl | F |
| 227 | H | i-butyl | n-propyl | cyclopropyl | F |
| 228 | H | i-butyl | n-propyl | CH₂-cyclopropyl | F |
| 229 | H | i-butyl | n-propyl | 2-tetrahydrofuranyl | F |
| 230 | H | i-butyl | n-propyl | CH₂-2-tetrahydrofuran | F |
| 231 | H | i-butyl | n-propyl | 2-tetrahydrothienyl | F |
| 232 | H | i-butyl | n-propyl | CH₂OCH₃ | Cl |
| 233 | H | i-butyl | n-propyl | CH₃ | Cl |
| 234 | H | i-butyl | n-propyl | CH₂OH | Cl |
| 235 | H | i-butyl | n-propyl | CH₂N(CH₃)₂ | Cl |
| 236 | H | i-butyl | n-propyl | CH₂-N-piperdinyl | Cl |
| 237 | H | i-butyl | n-propyl | CH₂-N-morpholinyl | Cl |
| 238 | H | i-butyl | n-propyl | cyclopropyl | Cl |
| 239 | H | i-butyl | n-propyl | CH₂-cyclopropyl | Cl |
| 240 | H | i-butyl | n-propyl | 2-tetrahydrofuranyl | Cl |
| 241 | H | i-butyl | n-propyl | CH₂-2-tetrahydrofuran | Cl |
| 242 | H | i-butyl | n-propyl | 2-tetrahydrothienyl | Cl |
| 243 | H | i-butyl | n-propyl | CH₂OCH₃ | Br |
| 244 | H | i-butyl | n-propyl | CH₃ | Br |
| 245 | H | i-butyl | n-propyl | CH₂OH | Br |
| 246 | H | i-butyl | n-propyl | CH₂N(CH₃)₂ | Br |
| 247 | H | i-butyl | n-propyl | CH₂-N-piperdinyl | Br |
| 248 | H | i-butyl | n-propyl | CH₂-N-morpholinyl | Br |
| 249 | H | i-butyl | n-propyl | cyclopropyl | Br |
| 250 | H | i-butyl | n-propyl | CH₂-cyclopropyl | Br |
| 251 | H | i-butyl | n-propyl | 2-tetrahydrofuranyl | Br |
| 252 | H | i-butyl | n-propyl | CH₂-2-tetrahydrofuran | Br |
| 253 | H | i-butyl | n-propyl | 2-tetrahydrothienyl | Br |
| 254 | H | i-butyl | n-propyl | CH₂OCH₃ | I |
| 255 | H | i-butyl | n-propyl | CH₃ | I |
| 256 | H | i-butyl | n-propyl | CH₂OH | I |
| 257 | H | i-butyl | n-propyl | CH₂N(CH₃)₂ | I |
| 258 | H | i-butyl | n-propyl | CH₂-N-piperdinyl | I |
| 259 | H | i-butyl | n-propyl | CH₂-N-morpholinyl | I |
| 260 | H | i-butyl | n-propyl | cyclopropyl | I |
| 261 | H | i-butyl | n-propyl | CH₂-cyclopropyl | I |
| 262 | H | i-butyl | n-propyl | 2-tetrahydrofuranyl | I |
| 263 | H | i-butyl | n-propyl | CH₂-2-tetrahydrofuran | I |

| Ex.# | R | R¹ | R² | R³ | Y' |
|---|---|---|---|---|---|
| 264 | H | i-butyl | n-propyl | 2-tetrahydrothienyl | I |
| 265 | H | cyclobutyl | n-propyl | $CH_2OCH_3$ | H |
| 266 | H | cyclobutyl | n-propyl | $CH_3$ | H |
| 267 | H | cyclobutyl | n-propyl | $CH_2OH$ | H |
| 268 | H | cyclobutyl | n-propyl | $CH_2N(CH_3)_2$ | H |
| 269 | H | cyclobutyl | n-propyl | $CH_2$-N-piperdinyl | H |
| 270 | H | cyclobutyl | n-propyl | $CH_2$-N-morpholinyl | H |
| 271 | H | cyclobutyl | n-propyl | cyclopropyl | H |
| 272 | H | cyclobutyl | n-propyl | $CH_2$-cyclopropyl | H |
| 273 | H | cyclobutyl | n-propyl | 2-tetrahydrofuranyl | H |
| 274 | H | cyclobutyl | n-propyl | $CH_2$-2-tetrahydrofuran | H |
| 275 | H | cyclobutyl | n-propyl | 2-tetrahydrothienyl | H |
| 276 | H | cyclobutyl | n-propyl | $CH_2OCH_3$ | $CF_3$ |
| 277 | H | cyclobutyl | n-propyl | $CH_3$ | $CF_3$ |
| 278 | H | cyclobutyl | n-propyl | $CH_2OH$ | $CF_3$ |
| 279 | H | cyclobutyl | n-propyl | $CH_2N(CH_3)_2$ | $CF_3$ |
| 280 | H | cyclobutyl | n-propyl | $CH_2$-N-piperdinyl | $CF_3$ |
| 281 | H | cyclobutyl | n-propyl | $CH_2$-N-morpholinyl | $CF_3$ |
| 282 | H | cyclobutyl | n-propyl | cyclopropyl | $CF_3$ |
| 283 | H | cyclobutyl | n-propyl | $CH_2$-cyclopropyl | $CF_3$ |
| 284 | H | cyclobutyl | n-propyl | 2-tetrahydrofuranyl | $CF_3$ |
| 285 | H | cyclobutyl | n-propyl | $CH_2$-2-tetrahydrofuran | $CF_3$ |
| 286 | H | cyclobutyl | n-propyl | 2-tetrahydrothienyl | $CF_3$ |
| 287 | H | cyclobutyl | n-propyl | $CH_2OCH_3$ | F |
| 288 | H | cyclobutyl | n-propyl | $CH_3$ | F |
| 289 | H | cyclobutyl | n-propyl | $CH_2OH$ | F |
| 290 | H | cyclobutyl | n-propyl | $CH_2N(CH_3)_2$ | F |
| 291 | H | cyclobutyl | n-propyl | $CH_2$-N-piperdinyl | F |
| 292 | H | cyclobutyl | n-propyl | $CH_2$-N-morpholinyl | F |
| 293 | H | cyclobutyl | n-propyl | cyclopropyl | F |
| 294 | H | cyclobutyl | n-propyl | $CH_2$-cyclopropyl | F |
| 295 | H | cyclobutyl | n-propyl | 2-tetrahydrofuranyl | F |
| 296 | H | cyclobutyl | n-propyl | $CH_2$-2-tetrahydrofuran | F |
| 297 | H | cyclobutyl | n-propyl | 2-tetrahydrothienyl | F |
| 298 | H | cyclobutyl | n-propyl | $CH_2OCH_3$ | Cl |
| 299 | H | cyclobutyl | n-propyl | $CH_3$ | Cl |
| 300 | H | cyclobutyl | n-propyl | $CH_2OH$ | Cl |
| 301 | H | cyclobutyl | n-propyl | $CH_2N(CH_3)_2$ | Cl |
| 302 | H | cyclobutyl | n-propyl | $CH_2$-N-piperdinyl | Cl |
| 303 | H | cyclobutyl | n-propyl | $CH_2$-N-morpholinyl | Cl |
| 304 | H | cyclobutyl | n-propyl | cyclopropyl | Cl |
| 305 | H | cyclobutyl | n-propyl | $CH_2$-cyclopropyl | Cl |
| 306 | H | cyclobutyl | n-propyl | 2-tetrahydrofuranyl | Cl |
| 307 | H | cyclobutyl | n-propyl | $CH_2$-2-tetrahydrofuran | Cl |
| 308 | H | cyclobutyl | n-propyl | 2-tetrahydrothienyl | Cl |
| 309 | H | cyclobutyl | n-propyl | $CH_2OCH_3$ | Br |
| 310 | H | cyclobutyl | n-propyl | $CH_3$ | Br |
| 311 | H | cyclobutyl | n-propyl | $CH_2OH$ | Br |
| 312 | H | cyclobutyl | n-propyl | $CH_2N(CH_3)_2$ | Br |
| 313 | H | cyclobutyl | n-propyl | $CH_2$-N-piperdinyl | Br |
| 314 | H | cyclobutyl | n-propyl | $CH_2$-N-morpholinyl | Br |
| 315 | H | cyclobutyl | n-propyl | cyclopropyl | Br |
| 316 | H | cyclobutyl | n-propyl | $CH_2$-cyclopropyl | Br |
| 317 | H | cyclobutyl | n-propyl | 2-tetrahydrofuranyl | Br |
| 318 | H | cyclobutyl | n-propyl | $CH_2$-2-tetrahydrofuran | Br |
| 319 | H | cyclobutyl | n-propyl | 2-tetrahydrothienyl | Br |
| 320 | H | cyclobutyl | n-propyl | $CH_2OCH_3$ | I |
| 321 | H | cyclobutyl | n-propyl | $CH_3$ | I |
| 322 | H | cyclobutyl | n-propyl | $CH_2OH$ | I |
| 323 | H | cyclobutyl | n-propyl | $CH_2N(CH_3)_2$ | I |
| 324 | H | cyclobutyl | n-propyl | $CH_2$-N-piperdinyl | I |
| 325 | H | cyclobutyl | n-propyl | $CH_2$-N-morpholinyl | I |
| 326 | H | cyclobutyl | n-propyl | cyclopropyl | I |
| 327 | H | cyclobutyl | n-propyl | $CH_2$-cyclopropyl | I |
| 328 | H | cyclobutyl | n-propyl | 2-tetrahydrofuranyl | I |
| 329 | H | cyclobutyl | n-propyl | $CH_2$-2-tetrahydrofuran | I |
| 330 | H | cyclobutyl | n-propyl | 2-tetrahydrothienyl | I |
| 331 | H | cyclopropylmethyl- | n-propyl | $CH_2OCH_3$ | H |
| 332 | H | cyclopropylmethyl- | n-propyl | $CH_3$ | H |
| 333 | H | cyclopropylmethyl- | n-propyl | $CH_2OH$ | H |
| 334 | H | cyclopropylmethyl- | n-propyl | $CH_2N(CH_3)_2$ | H |
| 335 | H | cyclopropylmethyl- | n-propyl | $CH_2$-N-piperdinyl | H |
| 336 | H | cyclopropylmethyl- | n-propyl | $CH_2$-N-morpholinyl | H |
| 337 | H | cyclopropylmethyl- | n-propyl | cyclopropyl | H |
| 338 | H | cyclopropylmethyl- | n-propyl | $CH_2$-cyclopropyl | H |
| 339 | H | cyclopropylmethyl- | n-propyl | 2-tetrahydrofuranyl | H |
| 340 | H | cyclopropylmethyl- | n-propyl | $CH_2$-2-tetrahydrofuran | H |
| 341 | H | cyclopropylmethyl- | n-propyl | 2-tetrahydrothienyl | H |
| 342 | H | cyclopropylmethyl- | n-propyl | $CH_2OCH_3$ | $CF_3$ |
| 343 | H | cyclopropylmethyl- | n-propyl | $CH_3$ | $CF_3$ |
| 344 | H | cyclopropylmethyl- | n-propyl | $CH_2OH$ | $CF_3$ |
| 345 | H | cyclopropylmethyl- | n-propyl | $CH_2N(CH_3)_2$ | $CF_3$ |
| 346 | H | cyclopropylmethyl- | n-propyl | $CH_2$-N-piperdinyl | $CF_3$ |
| 347 | H | cyclopropylmethyl- | n-propyl | $CH_2$-N-morpholinyl | $CF_3$ |
| 348 | H | cyclopropylmethyl- | n-propyl | cyclopropyl | $CF_3$ |
| 349 | H | cyclopropylmethyl- | n-propyl | $CH_2$-cyclopropyl | $CF_3$ |
| 350 | H | cyclopropylmethyl- | n-propyl | 2-tetrahydrofuranyl | $CF_3$ |
| 351 | H | cyclopropylmethyl- | n-propyl | $CH_2$-2-tetrahydrofuran | $CF_3$ |
| 352 | H | cyclopropylmethyl- | n-propyl | 2-tetrahydrothienyl | $CF_3$ |
| 353 | H | cyclopropylmethyl- | n-propyl | $CH_2OCH_3$ | F |
| 354 | H | cyclopropylmethyl- | n-propyl | $CH_3$ | F |
| 355 | H | cyclopropylmethyl- | n-propyl | $CH_2OH$ | F |
| 356 | H | cyclopropylmethyl- | n-propyl | $CH_2N(CH_3)_2$ | F |
| 357 | H | cyclopropylmethyl- | n-propyl | $CH_2$-N-piperdinyl | F |
| 358 | H | cyclopropylmethyl- | n-propyl | $CH_2$-N-morpholinyl | F |
| 359 | H | cyclopropylmethyl- | n-propyl | cyclopropyl | F |
| 360 | H | cyclopropylmethyl- | n-propyl | $CH_2$-cyclopropyl | F |
| 361 | H | cyclopropylmethyl- | n-propyl | 2-tetrahydrofuranyl | F |
| 362 | H | cyclopropylmethyl- | n-propyl | $CH_2$-2-tetrahydrofuran | F |
| 363 | H | cyclopropylmethyl- | n-propyl | 2-tetrahydrothienyl | F |
| 364 | H | cyclopropylmethyl- | n-propyl | $CH_2OCH_3$ | Cl |
| 365 | H | cyclopropylmethyl- | n-propyl | $CH_3$ | Cl |
| 366 | H | cyclopropylmethyl- | n-propyl | $CH_2OH$ | Cl |
| 367 | H | cyclopropylmethyl- | n-propyl | $CH_2N(CH_3)_2$ | Cl |
| 368 | H | cyclopropylmethyl- | n-propyl | $CH_2$-N-piperdinyl | Cl |
| 369 | H | cyclopropylmethyl- | n-propyl | $CH_2$-N-morpholinyl | Cl |
| 370 | H | cyclopropylmethyl- | n-propyl | cyclopropyl | Cl |
| 371 | H | cyclopropylmethyl- | n-propyl | $CH_2$-cyclopropyl | Cl |
| 372 | H | cyclopropylmethyl- | n-propyl | 2-tetrahydrofuranyl | Cl |
| 373 | H | cyclopropylmethyl- | n-propyl | $CH_2$-2-tetrahydrofuran | Cl |
| 374 | H | cyclopropylmethyl- | n-propyl | 2-tetrahydrothienyl | Cl |
| 375 | H | cyclopropylmethyl- | n-propyl | $CH_2OCH_3$ | Br |
| 376 | H | cyclopropylmethyl- | n-propyl | $CH_3$ | Br |
| 377 | H | cyclopropylmethyl- | n-propyl | $CH_2OH$ | Br |
| 378 | H | cyclopropylmethyl- | n-propyl | $CH_2N(CH_3)_2$ | Br |
| 379 | H | cyclopropylmethyl- | n-propyl | $CH_2$-N-piperdinyl | Br |
| 380 | H | cyclopropylmethyl- | n-propyl | $CH_2$-N-morpholinyl | Br |
| 381 | H | cyclopropylmethyl- | n-propyl | cyclopropyl | Br |
| 382 | H | cyclopropylmethyl- | n-propyl | $CH_2$-cyclopropyl | Br |
| 383 | H | cyclopropylmethyl- | n-propyl | 2-tetrahydrofuranyl | Br |
| 384 | H | cyclopropylmethyl- | n-propyl | $CH_2$-2-tetrahydrofuran | Br |
| 385 | H | cyclopropylmethyl- | n-propyl | 2-tetrahydrothienyl | Br |
| 386 | H | cyclopropylmethyl- | n-propyl | $CH_2OCH_3$ | I |
| 387 | H | cyclopropylmethyl- | n-propyl | $CH_3$ | I |
| 388 | H | cyclopropylmethyl- | n-propyl | $CH_2OH$ | I |
| 389 | H | cyclopropylmethyl- | n-propyl | $CH_2N(CH_3)_2$ | I |
| 390 | H | cyclopropylmethyl- | n-propyl | $CH_2$-N-piperdinyl | I |
| 391 | H | cyclopropylmethyl- | n-propyl | $CH_2$-N-morpholinyl | I |
| 392 | H | cyclopropylmethyl- | n-propyl | cyclopropyl | I |
| 393 | H | cyclopropylmethyl- | n-propyl | $CH_2$-cyclopropyl | I |
| 394 | H | cyclopropylmethyl- | n-propyl | 2-tetrahydrofuranyl | I |
| 395 | H | cyclopropylmethyl- | n-propyl | $CH_2$-2-tetrahydrofuran | I |
| 396 | H | cyclopropylmethyl- | n-propyl | 2-tetrahydrothienyl | I | or a pharmaceutically acceptable salt thereof.

10. A method for inhibiting, relieving and/or ameliorating ischemia/reprefusion injuries in a mammal, comprising administering to the mammal an effective amount of a compound of formula I or a stereoisomer or a pharmaceutically acceptable salt thereof:

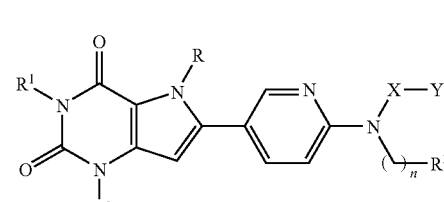

wherein:

R is selected from: H, OH, $C_{1-6}$ alkyl, halo-$C_{1-8}$ alkyl, $C_{3-6}$ alkenyl, $C_{3-6}$ alkynyl, ($C_{3-8}$ cycloalkyl)$C_{1-8}$ alkylene, ($C_{4-10}$ heterocycle)$C_{1-8}$ alkylene, ($C_{6-10}$ aryl)$C_{1-8}$ alkylene, and ($C_{5-10}$ heteroaryl)$C_{1-8}$ alkylene, wherein R optionally is substituted with 1 $R^d$;

$R^d$ is independently selected from: F, Cl, Br, I, $C_{1-6}$ alkyl, $C_{2-6}$ alkenyl, $C_{2-6}$ alkynyl, $OC_{1-6}$ alkyl, $NO_2$, —CN, $CF_3$, and $OCF_3$;

$R^1$ and $R^2$ are independently selected from: H, $C_{1-8}$ alkyl, $C_{3-8}$ alkenyl, $C_{3-8}$ alkynyl, $C_{1-8}$ alkoxy, $C_{3-8}$ cycloalkyl, ($C_{3-8}$ cycloalkyl)$C_{1-8}$ alkylene, $C_{4-10}$ heterocycle, ($C_{4-10}$ heterocycle)$C_{1-8}$ alkylene, $C_{6-10}$ aryl, ($C_{6-10}$ aryl)$C_{1-8}$ alkylene, $C_{5-10}$ heteroaryl, and ($C_{5-10}$ heteroaryl)$C_{1-8}$ alkylene, wherein $R^1$ and $R^2$ are independently optionally substituted with 1-2 $R^{1a}$;

$R^{1a}$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_nNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

$R^a$ is independently selected from: H, $C_{1-6}$ alkyl, $C_{2-6}$ alkenyl, $C_{2-6}$ alkynyl, $C_{3-8}$ cycloalkyl, ($C_{3-8}$ cycloalkyl)$C_{1-8}$ alkylene, $C_{4-10}$ heterocycle, ($C_{4-10}$ heterocycle)$C_{1-8}$ alkylene, $C_{6-10}$ aryl, ($C_{6-10}$ aryl)$C_{1-8}$ alkylene, $C_{5-10}$ heteroaryl, and ($C_{5-10}$ heteroaryl)$C_{1-8}$ alkylene, wherein the alkyl is optionally interrupted with 1-2 heteroatoms selected from the group consisting of —O—, —$S(O)_p$— and —$NR^b$—;

$R^b$ is independently selected from the group consisting of H, $C_{1-6}$ alkyl, and benzyl;

$R^3$ is selected from: OH, $C_{1-8}$ alkoxy, $NR^{3a}R^{3b}$, $C_{3-8}$ cycloalkyl, $C_{4-10}$ heterocycle, $C_{6-10}$ aryl, and $C_{5-10}$ heteroaryl, wherein the cycloalkyl, heterocycle, aryl, and heteroaryl are optionally substituted with 1-2 $R^{3c}$;

$R^{3a}$ and $R^{3b}$ are independently selected from: $C_{1-8}$ alkyl, $C_{2-8}$ alkenyl, $C_{2-8}$ alkynyl, phenyl, and benzyl;

$R^{3c}$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

X is selected from: $(CH_2)_q$, $(CH_2)_rC(O)$, and $(CH_2)_rC(O)NR^4$;

$R^4$ is selected from: H, $C_{1-4}$ alkyl, $C_{1-4}$ alkoxy, and $C_{1-4}$ haloalkyl;

Y is selected from: 5-10 membered heteroaryl and 6-10 membered aryl, wherein Y is optionally substituted with 1-4 $Y^1$;

$Y^1$ is independently selected from: F, Cl, Br, I, $C_{1-6}$ alkyl, $C_{2-6}$ alkenyl, $C_{2-6}$ alkynyl, —$(CH_2)_aOR^a$, —$(CH_2)_aNR^aR^a$, —$(CH_2)_aNHOH$, —$(CH_2)_aNR^aNR^aR^a$, —$(CH_2)_aNO_2$, —$(CH_2)_aCN$, —$(CH_2)_aCO_2R^a$, —$(CH_2)_aC(O)R^a$, —$(CH_2)_aOC(O)R^a$, —$(CH_2)_aCONR^aR^a$, $CF_3$, and $OCF_3$;

a is independently selected from the group consisting of 0, 1, and 2;

n is independently selected from: 1, 2, and 3;

p is independently selected from: 0, 1, and 2;

q is independently selected from 1, 2, 3, and 4; and, r is independently selected from 0, 1, 2, and 3.

11. The method according to claim 10, wherein the compound is of formula II or a stereoisomer or a pharmaceutically acceptable salt thereof:

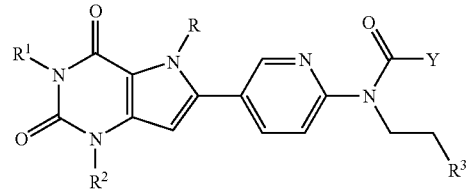

wherein:

R is selected from: H and $C_{1-4}$ alkyl;

$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl)$C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;

$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle are optionally substituted with 1-2 $R^{3c}$;

$R^{3a}$ and $R^{3b}$ are independently selected from: $C_{1-4}$ alkyl, phenyl, and benzyl;

$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;

Y is selected from: 5-6 membered heteroaryl and phenyl, wherein Y is optionally substituted with 1-2 $Y^1$;

$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and, $R^a$ is independently selected from: H, $C_{1-4}$ alkyl, $C_{3-6}$ cycloalkyl, phenyl, and benzyl.

12. The method according to claim 11, wherein:

R is H;

$R^1$ and $R^2$ are independently selected from: n-propyl, cyclopropylmethyl, and cyclobutyl;

$R^3$ is selected from: cyclopropyl, cyclobutyl, N-pyrrolidino, N-piperidino, N-piperazino, and N-morpholino;

Y is selected from: pyridyl and pyrimidyl, wherein Y is optionally substituted with 1-2 $Y^1$; and, $Y^1$ is independently selected from: F, Cl, $CH_3$, $OCH_3$, $NO_2$, —CN, and $CF_3$.

13. The method according to claim 12, wherein:

$R^1$ is selected from: n-propyl and cyclopropylmethyl; and, $R^2$ is n-propyl.

14. The method according to claim 12, wherein:

$R^1$ is n-propyl; and, $R^2$ is n-propyl.

15. The method according to claim 10, wherein the compound is of formula IV or a stereoisomer or a pharmaceutically acceptable salt thereof:

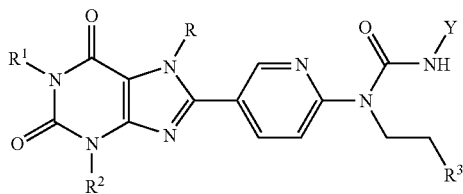

IV wherein:
R is selected from: H and $C_{1-4}$ alkyl;
$R^1$ and $R^2$ are independently selected from: H, $C_{1-4}$ alkyl, $C_{3-4}$ alkenyl, $C_{3-4}$ alkynyl, $C_{3-6}$ cycloalkyl, ($C_{3-6}$ cycloalkyl)$C_{1-2}$ alkylene, $C_{5-6}$ heterocycle, ($C_{5-6}$ heterocycle)$C_{1-2}$ alkylene, $C_{6-10}$ aryl, ($C_{6-10}$ aryl)$C_{1-2}$ alkylene, $C_{5-10}$ heteroaryl, and ($C_{5-10}$ heteroaryl)$C_{1-2}$ alkylene, wherein $R^1$ and $R^2$ are independently optionally substituted with 1-2 $R^{1a}$;
$R^{1a}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;
$R^3$ is selected from: $OCH_3$, $OCH_2CH_3$, $NR^{3a}R^{3b}$, $C_{3-6}$ cycloalkyl, and $C_{5-6}$ heterocycle, wherein the cycloalkyl and heterocycle are optionally substituted with 1-2 $R^{3c}$;
$R^{3a}$ and $R^{3b}$ are independently selected from: $C_{1-4}$ alkyl, phenyl, and benzyl;
$R^{3c}$ is independently selected from: F, Cl, Br, I, $C_{1-4}$ alkyl, $OR^a$, $NR^aR^a$, $NO_2$, —CN, $CO_2R^a$, $C(O)R^a$, $OC(O)R^a$, $CONR^aR^a$, $CF_3$, and $OCF_3$;
Y is selected from: 5-6 membered heteroaryl and phenyl, wherein Y is optionally substituted with 1-2 $Y^1$;
$Y^1$ is independently selected from: F, Cl, Br, I, $C_{1-4}$ alkyl, $C_{2-4}$ alkenyl, $C_{2-4}$ alkynyl, $OR^a$, $NR^aR^a$, $NO_2$, —CN, $CO_2R^a$, $C(O)R^a$, $OC(O)R^a$, $CONR^aR^a$, $CF_3$, and $OCF_3$; and,
$R^a$ is independently selected from: H, $C_{1-4}$ alkyl, $C_{3-6}$ cycloalkyl, phenyl, and benzyl.

16. The method according to claim 10, wherein the compound is of formula V or VI or stereoisomer or a pharmaceutically acceptable salt thereof:

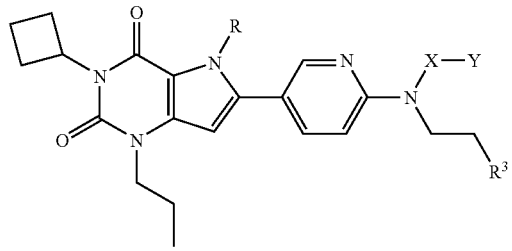

V

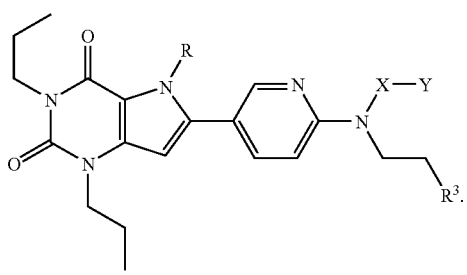

VI

17. The method according to claim 10, wherein the compound is:

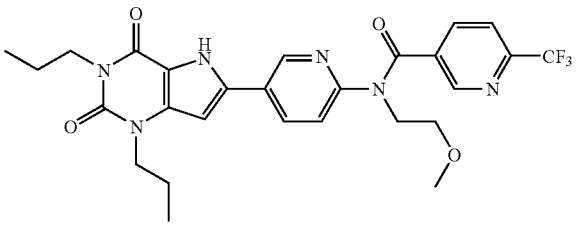 [SMILES: CCCn1c(=O)c2[nH]c(-c3ccc(N(CCOC)C(=O)c4ccc(C(F)(F)F)nc4)nc3)cc2n(CCC)c1=O]

or a pharmaceutically acceptable salt thereof.

18. The method according to claim 10, wherein the compound is selected from

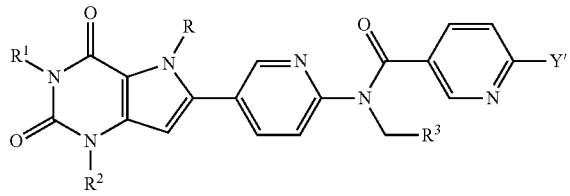

or

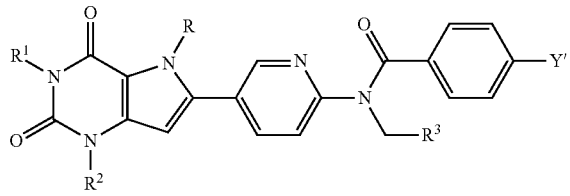

wherein R, $R^1$, $R^2$, $R^3$ and Y' are as defined in the following table:

| Ex.# | R | $R^1$ | $R^2$ | $R^3$ | Y' |
|---|---|---|---|---|---|
| 1 | H | n-propyl | n-propyl | $CH_2OCH_3$ | H |
| 2 | H | n-propyl | n-propyl | $CH_3$ | H |
| 3 | H | n-propyl | n-propyl | $CH_2OH$ | H |
| 4 | H | n-propyl | n-propyl | $CH_2N(CH_3)_2$ | H |
| 5 | H | n-propyl | n-propyl | $CH_2$-N-piperdinyl | H |
| 6 | H | n-propyl | n-propyl | $CH_2$-N-morpholinyl | H |
| 7 | H | n-propyl | n-propyl | cyclopropyl | H |
| 8 | H | n-propyl | n-propyl | $CH_2$-cyclopropyl | H |
| 9 | H | n-propyl | n-propyl | 2-tetrahydrofuranyl | H |
| 10 | H | n-propyl | n-propyl | $CH_2$-2-tetrahydrofuran | H |
| 11 | H | n-propyl | n-propyl | 2-tetrahydrothienyl | H |
| 12 | H | n-propyl | n-propyl | $CH_2OCH_3$ | $CF_3$ |
| 13 | H | n-propyl | n-propyl | $CH_3$ | $CF_3$ |
| 14 | H | n-propyl | n-propyl | $CH_2OH$ | $CF_3$ |
| 15 | H | n-propyl | n-propyl | $CH_2N(CH_3)_2$ | $CF_3$ |
| 16 | H | n-propyl | n-propyl | $CH_2$-N-piperdinyl | $CF_3$ |
| 17 | H | n-propyl | n-propyl | $CH_2$-N-morpholinyl | $CF_3$ |
| 18 | H | n-propyl | n-propyl | cyclopropyl | $CF_3$ |
| 19 | H | n-propyl | n-propyl | $CH_2$-cyclopropyl | $CF_3$ |
| 20 | H | n-propyl | n-propyl | 2-tetrahydrofuranyl | $CF_3$ |
| 21 | H | n-propyl | n-propyl | $CH_2$-2-tetrahydrofuran | $CF_3$ |
| 22 | H | n-propyl | n-propyl | 2-tetrahydrothienyl | $CF_3$ |
| 23 | H | n-propyl | n-propyl | $CH_2OCH_3$ | F |
| 24 | H | n-propyl | n-propyl | $CH_3$ | F |
| 25 | H | n-propyl | n-propyl | $CH_2OH$ | F |
| 26 | H | n-propyl | n-propyl | $CH_2N(CH_3)_2$ | F |
| 27 | H | n-propyl | n-propyl | $CH_2$-N-piperdinyl | F |
| 28 | H | n-propyl | n-propyl | $CH_2$-N-morpholinyl | F |
| 29 | H | n-propyl | n-propyl | cyclopropyl | F |

-continued

| Ex.# | R | R¹ | R² | R³ | Y' |
|---|---|---|---|---|---|
| 30 | H | n-propyl | n-propyl | CH₂-cyclopropyl | F |
| 31 | H | n-propyl | n-propyl | 2-tetrahydrofuranyl | F |
| 32 | H | n-propyl | n-propyl | CH₂-2-tetrahydrofuran | F |
| 33 | H | n-propyl | n-propyl | 2-tetrahydrothienyl | F |
| 34 | H | n-propyl | n-propyl | CH₂OCH₃ | Cl |
| 35 | H | n-propyl | n-propyl | CH₃ | Cl |
| 36 | H | n-propyl | n-propyl | CH₂OH | Cl |
| 37 | H | n-propyl | n-propyl | CH₂N(CH₃)₂ | Cl |
| 38 | H | n-propyl | n-propyl | CH₂-N-piperdinyl | Cl |
| 39 | H | n-propyl | n-propyl | CH₂-N-morpholinyl | Cl |
| 40 | H | n-propyl | n-propyl | cyclopropyl | Cl |
| 41 | H | n-propyl | n-propyl | CH₂-cyclopropyl | Cl |
| 42 | H | n-propyl | n-propyl | 2-tetrahydrofuranyl | Cl |
| 43 | H | n-propyl | n-propyl | CH₂-2-tetrahydrofuran | Cl |
| 44 | H | n-propyl | n-propyl | 2-tetrahydrothienyl | Cl |
| 45 | H | n-propyl | n-propyl | CH₂OCH₃ | Br |
| 46 | H | n-propyl | n-propyl | CH₃ | Br |
| 47 | H | n-propyl | n-propyl | CH₂OH | Br |
| 48 | H | n-propyl | n-propyl | CH₂N(CH₃)₂ | Br |
| 49 | H | n-propyl | n-propyl | CH₂-N-piperdinyl | Br |
| 50 | H | n-propyl | n-propyl | CH₂-N-morpholinyl | Br |
| 51 | H | n-propyl | n-propyl | cyclopropyl | Br |
| 52 | H | n-propyl | n-propyl | CH₂-cyclopropyl | Br |
| 53 | H | n-propyl | n-propyl | 2-tetrahydrofuranyl | Br |
| 54 | H | n-propyl | n-propyl | CH₂-2-tetrahydrofuran | Br |
| 55 | H | n-propyl | n-propyl | 2-tetrahydrothienyl | Br |
| 56 | H | n-propyl | n-propyl | CH₂OCH₃ | I |
| 57 | H | n-propyl | n-propyl | CH₃ | I |
| 58 | H | n-propyl | n-propyl | CH₂OH | I |
| 59 | H | n-propyl | n-propyl | CH₂N(CH₃)₂ | I |
| 60 | H | n-propyl | n-propyl | CH₂-N-piperdinyl | I |
| 61 | H | n-propyl | n-propyl | CH₂-N-morpholinyl | I |
| 62 | H | n-propyl | n-propyl | cyclopropyl | I |
| 63 | H | n-propyl | n-propyl | CH₂-cyclopropyl | I |
| 64 | H | n-propyl | n-propyl | 2-tetrahydrofuranyl | I |
| 65 | H | n-propyl | n-propyl | CH₂-2-tetrahydrofuran | I |
| 66 | H | n-propyl | n-propyl | 2-tetrahydrothienyl | I |
| 67 | H | i-propyl | n-propyl | CH₂OCH₃ | H |
| 68 | H | i-propyl | n-propyl | CH₃ | H |
| 69 | H | i-propyl | n-propyl | CH₂OH | H |
| 70 | H | i-propyl | n-propyl | CH₂N(CH₃)₂ | H |
| 71 | H | i-propyl | n-propyl | CH₂-N-piperdinyl | H |
| 72 | H | i-propyl | n-propyl | CH₂-N-morpholinyl | H |
| 73 | H | i-propyl | n-propyl | cyclopropyl | H |
| 74 | H | i-propyl | n-propyl | CH₂-cyclopropyl | H |
| 75 | H | i-propyl | n-propyl | 2-tetrahydrofuranyl | H |
| 76 | H | i-propyl | n-propyl | CH₂-2-tetrahydrofuran | H |
| 77 | H | i-propyl | n-propyl | 2-tetrahydrothienyl | H |
| 78 | H | i-propyl | n-propyl | CH₂OCH₃ | CF₃ |
| 79 | H | i-propyl | n-propyl | CH₃ | CF₃ |
| 80 | H | i-propyl | n-propyl | CH₂OH | CF₃ |
| 81 | H | i-propyl | n-propyl | CH₂N(CH₃)₂ | CF₃ |
| 82 | H | i-propyl | n-propyl | CH₂-N-piperdinyl | CF₃ |
| 83 | H | i-propyl | n-propyl | CH₂-N-morpholinyl | CF₃ |
| 84 | H | i-propyl | n-propyl | cyclopropyl | CF₃ |
| 85 | H | i-propyl | n-propyl | CH₂-cyclopropyl | CF₃ |
| 86 | H | i-propyl | n-propyl | 2-tetrahydrofuranyl | CF₃ |
| 87 | H | i-propyl | n-propyl | CH₂-2-tetrahydrofuran | CF₃ |
| 88 | H | i-propyl | n-propyl | 2-tetrahydrothienyl | CF₃ |
| 89 | H | i-propyl | n-propyl | CH₂OCH₃ | F |
| 90 | H | i-propyl | n-propyl | CH₃ | F |
| 91 | H | i-propyl | n-propyl | CH₂OH | F |
| 92 | H | i-propyl | n-propyl | CH₂N(CH₃)₂ | F |
| 93 | H | i-propyl | n-propyl | CH₂-N-piperdinyl | F |
| 94 | H | i-propyl | n-propyl | CH₂-N-morpholinyl | F |
| 95 | H | i-propyl | n-propyl | cyclopropyl | F |
| 96 | H | i-propyl | n-propyl | CH₂-cyclopropyl | F |
| 97 | H | i-propyl | n-propyl | 2-tetrahydrofuranyl | F |
| 98 | H | i-propyl | n-propyl | CH₂-2-tetrahydrofuran | F |
| 99 | H | i-propyl | n-propyl | 2-tetrahydrothienyl | F |
| 100 | H | i-propyl | n-propyl | CH₂OCH₃ | Cl |
| 101 | H | i-propyl | n-propyl | CH₃ | Cl |
| 102 | H | i-propyl | n-propyl | CH₂OH | Cl |
| 103 | H | i-propyl | n-propyl | CH₂N(CH₃)₂ | Cl |
| 104 | H | i-propyl | n-propyl | CH₂-N-piperdinyl | Cl |
| 105 | H | i-propyl | n-propyl | CH₂-N-morpholinyl | Cl |
| 106 | H | i-propyl | n-propyl | cyclopropyl | Cl |
| 107 | H | i-propyl | n-propyl | CH₂-cyclopropyl | Cl |
| 108 | H | i-propyl | n-propyl | 2-tetrahydrofuranyl | Cl |
| 109 | H | i-propyl | n-propyl | CH₂-2-tetrahydrofuran | Cl |
| 110 | H | i-propyl | n-propyl | 2-tetrahydrothienyl | Cl |
| 111 | H | i-propyl | n-propyl | CH₂OCH₃ | Br |
| 112 | H | i-propyl | n-propyl | CH₃ | Br |
| 113 | H | i-propyl | n-propyl | CH₂OH | Br |
| 114 | H | i-propyl | n-propyl | CH₂N(CH₃)₂ | Br |
| 115 | H | i-propyl | n-propyl | CH₂-N-piperdinyl | Br |
| 116 | H | i-propyl | n-propyl | CH₂-N-morpholinyl | Br |
| 117 | H | i-propyl | n-propyl | cyclopropyl | Br |
| 118 | H | i-propyl | n-propyl | CH₂-cyclopropyl | Br |
| 119 | H | i-propyl | n-propyl | 2-tetrahydrofuranyl | Br |
| 120 | H | i-propyl | n-propyl | CH₂-2-tetrahydrofuran | Br |
| 121 | H | i-propyl | n-propyl | 2-tetrahydrothienyl | Br |
| 122 | H | i-propyl | n-propyl | CH₂OCH₃ | I |
| 123 | H | i-propyl | n-propyl | CH₃ | I |
| 124 | H | i-propyl | n-propyl | CH₂OH | I |
| 125 | H | i-propyl | n-propyl | CH₂N(CH₃)₂ | I |
| 126 | H | i-propyl | n-propyl | CH₂-N-piperdinyl | I |
| 127 | H | i-propyl | n-propyl | CH₂-N-morpholinyl | I |
| 128 | H | i-propyl | n-propyl | cyclopropyl | I |
| 129 | H | i-propyl | n-propyl | CH₂-cyclopropyl | I |
| 130 | H | i-propyl | n-propyl | 2-tetrahydrofuranyl | I |
| 131 | H | i-propyl | n-propyl | CH₂-2-tetrahydrofuran | I |
| 132 | H | i-propyl | n-propyl | 2-tetrahydrothienyl | I |
| 133 | H | n-butyl | n-propyl | CH₂OCH₃ | H |
| 134 | H | n-butyl | n-propyl | CH₃ | H |
| 135 | H | n-butyl | n-propyl | CH₂OH | H |
| 136 | H | n-butyl | n-propyl | CH₂N(CH₃)₂ | H |
| 137 | H | n-butyl | n-propyl | CH₂-N-piperdinyl | H |
| 138 | H | n-butyl | n-propyl | CH₂-N-morpholinyl | H |
| 139 | H | n-butyl | n-propyl | cyclopropyl | H |
| 140 | H | n-butyl | n-propyl | CH₂-cyclopropyl | H |
| 141 | H | n-butyl | n-propyl | 2-tetrahydrofuranyl | H |
| 142 | H | n-butyl | n-propyl | CH₂-2-tetrahydrofuran | H |
| 143 | H | n-butyl | n-propyl | 2-tetrahydrothienyl | H |
| 144 | H | n-butyl | n-propyl | CH₂OCH₃ | CF₃ |
| 145 | H | n-butyl | n-propyl | CH₃ | CF₃ |
| 146 | H | n-butyl | n-propyl | CH₂OH | CF₃ |
| 147 | H | n-butyl | n-propyl | CH₂N(CH₃)₂ | CF₃ |
| 148 | H | n-butyl | n-propyl | CH₂-N-piperdinyl | CF₃ |
| 149 | H | n-butyl | n-propyl | CH₂-N-morpholinyl | CF₃ |
| 150 | H | n-butyl | n-propyl | cyclopropyl | CF₃ |
| 151 | H | n-butyl | n-propyl | CH₂-cyclopropyl | CF₃ |
| 152 | H | n-butyl | n-propyl | 2-tetrahydrofuranyl | CF₃ |
| 153 | H | n-butyl | n-propyl | CH₂-2-tetrahydrofuran | CF₃ |
| 154 | H | n-butyl | n-propyl | 2-tetrahydrothienyl | CF₃ |
| 155 | H | n-butyl | n-propyl | CH₂OCH₃ | F |
| 156 | H | n-butyl | n-propyl | CH₃ | F |
| 157 | H | n-butyl | n-propyl | CH₂OH | F |
| 158 | H | n-butyl | n-propyl | CH₂N(CH₃)₂ | F |
| 159 | H | n-butyl | n-propyl | CH₂-N-piperdinyl | F |
| 160 | H | n-butyl | n-propyl | CH₂-N-morpholinyl | F |
| 161 | H | n-butyl | n-propyl | cyclopropyl | F |
| 162 | H | n-butyl | n-propyl | CH₂-cyclopropyl | F |
| 163 | H | n-butyl | n-propyl | 2-tetrahydrofuranyl | F |
| 164 | H | n-butyl | n-propyl | CH₂-2-tetrahydrofuran | F |
| 165 | H | n-butyl | n-propyl | 2-tetrahydrothienyl | F |
| 166 | H | n-butyl | n-propyl | CH₂OCH₃ | Cl |
| 167 | H | n-butyl | n-propyl | CH₃ | Cl |
| 168 | H | n-butyl | n-propyl | CH₂OH | Cl |
| 169 | H | n-butyl | n-propyl | CH₂N(CH₃)₂ | Cl |
| 170 | H | n-butyl | n-propyl | CH₂-N-piperdinyl | Cl |
| 171 | H | n-butyl | n-propyl | CH₂-N-morpholinyl | Cl |
| 172 | H | n-butyl | n-propyl | cyclopropyl | Cl |
| 173 | H | n-butyl | n-propyl | CH₂-cyclopropyl | Cl |
| 174 | H | n-butyl | n-propyl | 2-tetrahydrofuranyl | Cl |
| 175 | H | n-butyl | n-propyl | CH₂-2-tetrahydrofuran | Cl |
| 176 | H | n-butyl | n-propyl | 2-tetrahydrothienyl | Cl |
| 177 | H | n-butyl | n-propyl | CH₂OCH₃ | Br |
| 178 | H | n-butyl | n-propyl | CH₃ | Br |
| 179 | H | n-butyl | n-propyl | CH₂OH | Br |
| 180 | H | n-butyl | n-propyl | CH₂N(CH₃)₂ | Br |
| 181 | H | n-butyl | n-propyl | CH₂-N-piperdinyl | Br |
| 182 | H | n-butyl | n-propyl | CH₂-N-morpholinyl | Br |
| 183 | H | n-butyl | n-propyl | cyclopropyl | Br |
| 184 | H | n-butyl | n-propyl | CH₂-cyclopropyl | Br |
| 185 | H | n-butyl | n-propyl | 2-tetrahydrofuranyl | Br |

| Ex.# | R | R¹ | R² | R³ | Y' |
|---|---|---|---|---|---|
| 186 | H | n-butyl | n-propyl | CH₂-2-tetrahydrofuran | Br |
| 187 | H | n-butyl | n-propyl | 2-tetrahydrothienyl | Br |
| 188 | H | n-butyl | n-propyl | CH₂OCH₃ | I |
| 189 | H | n-butyl | n-propyl | CH₃ | I |
| 190 | H | n-butyl | n-propyl | CH₂OH | I |
| 191 | H | n-butyl | n-propyl | CH₂N(CH₃)₂ | I |
| 192 | H | n-butyl | n-propyl | CH₂-N-piperdinyl | I |
| 193 | H | n-butyl | n-propyl | CH₂-N-morpholinyl | I |
| 194 | H | n-butyl | n-propyl | cyclopropyl | I |
| 195 | H | n-butyl | n-propyl | CH₂-cyclopropyl | I |
| 196 | H | n-butyl | n-propyl | 2-tetrahydrofuranyl | I |
| 197 | H | n-butyl | n-propyl | CH₂-2-tetrahydrofuran | I |
| 198 | H | n-butyl | n-propyl | 2-tetrahydrothienyl | I |
| 199 | H | i-butyl | n-propyl | CH₂OCH₃ | H |
| 200 | H | i-butyl | n-propyl | CH₃ | H |
| 201 | H | i-butyl | n-propyl | CH₂OH | H |
| 202 | H | i-butyl | n-propyl | CH₂N(CH₃)₂ | H |
| 203 | H | i-butyl | n-propyl | CH₂-N-piperdinyl | H |
| 204 | H | i-butyl | n-propyl | CH₂-N-morpholinyl | H |
| 205 | H | i-butyl | n-propyl | cyclopropyl | H |
| 206 | H | i-butyl | n-propyl | CH₂-cyclopropyl | H |
| 207 | H | i-butyl | n-propyl | 2-tetrahydrofuranyl | H |
| 208 | H | i-butyl | n-propyl | CH₂-2-tetrahydrofuran | H |
| 209 | H | i-butyl | n-propyl | 2-tetrahydrothienyl | H |
| 210 | H | i-butyl | n-propyl | CH₂OCH₃ | CF₃ |
| 211 | H | i-butyl | n-propyl | CH₃ | CF₃ |
| 212 | H | i-butyl | n-propyl | CH₂OH | CF₃ |
| 213 | H | i-butyl | n-propyl | CH₂N(CH₃)₂ | CF₃ |
| 214 | H | i-butyl | n-propyl | CH₂-N-piperdinyl | CF₃ |
| 215 | H | i-butyl | n-propyl | CH₂-N-morpholinyl | CF₃ |
| 216 | H | i-butyl | n-propyl | cyclopropyl | CF₃ |
| 217 | H | i-butyl | n-propyl | CH₂-cyclopropyl | CF₃ |
| 218 | H | i-butyl | n-propyl | 2-tetrahydrofuranyl | CF₃ |
| 219 | H | i-butyl | n-propyl | CH₂-2-tetrahydrofuran | CF₃ |
| 220 | H | i-butyl | n-propyl | 2-tetrahydrothienyl | CF₃ |
| 221 | H | i-butyl | n-propyl | CH₂OCH₃ | F |
| 222 | H | i-butyl | n-propyl | CH₃ | F |
| 223 | H | i-butyl | n-propyl | CH₂OH | F |
| 224 | H | i-butyl | n-propyl | CH₂N(CH₃)₂ | F |
| 225 | H | i-butyl | n-propyl | CH₂-N-piperdinyl | F |
| 226 | H | i-butyl | n-propyl | CH₂-N-morpholinyl | F |
| 227 | H | i-butyl | n-propyl | cyclopropyl | F |
| 228 | H | i-butyl | n-propyl | CH₂-cyclopropyl | F |
| 229 | H | i-butyl | n-propyl | 2-tetrahydrofuranyl | F |
| 230 | H | i-butyl | n-propyl | CH₂-2-tetrahydrofuran | F |
| 231 | H | i-butyl | n-propyl | 2-tetrahydrothienyl | F |
| 232 | H | i-butyl | n-propyl | CH₂OCH₃ | Cl |
| 233 | H | i-butyl | n-propyl | CH₃ | Cl |
| 234 | H | i-butyl | n-propyl | CH₂OH | Cl |
| 235 | H | i-butyl | n-propyl | CH₂N(CH₃)₂ | Cl |
| 236 | H | i-butyl | n-propyl | CH₂-N-piperdinyl | Cl |
| 237 | H | i-butyl | n-propyl | CH₂-N-morpholinyl | Cl |
| 238 | H | i-butyl | n-propyl | cyclopropyl | Cl |
| 239 | H | i-butyl | n-propyl | CH₂-cyclopropyl | Cl |
| 240 | H | i-butyl | n-propyl | 2-tetrahydrofuranyl | Cl |
| 241 | H | i-butyl | n-propyl | CH₂-2-tetrahydrofuran | Cl |
| 242 | H | i-butyl | n-propyl | 2-tetrahydrothienyl | Cl |
| 243 | H | i-butyl | n-propyl | CH₂OCH₃ | Br |
| 244 | H | i-butyl | n-propyl | CH₃ | Br |
| 245 | H | i-butyl | n-propyl | CH₂OH | Br |
| 246 | H | i-butyl | n-propyl | CH₂N(CH₃)₂ | Br |
| 247 | H | i-butyl | n-propyl | CH₂-N-piperdinyl | Br |
| 248 | H | i-butyl | n-propyl | CH₂-N-morpholinyl | Br |
| 249 | H | i-butyl | n-propyl | cyclopropyl | Br |
| 250 | H | i-butyl | n-propyl | CH₂-cyclopropyl | Br |
| 251 | H | i-butyl | n-propyl | 2-tetrahydrofuranyl | Br |
| 252 | H | i-butyl | n-propyl | CH₂-2-tetrahydrofuran | Br |
| 253 | H | i-butyl | n-propyl | 2-tetrahydrothienyl | Br |
| 254 | H | i-butyl | n-propyl | CH₂OCH₃ | I |
| 255 | H | i-butyl | n-propyl | CH₃ | I |
| 256 | H | i-butyl | n-propyl | CH₂OH | I |
| 257 | H | i-butyl | n-propyl | CH₂N(CH₃)₂ | I |
| 258 | H | i-butyl | n-propyl | CH₂-N-piperdinyl | I |
| 259 | H | i-butyl | n-propyl | CH₂-N-morpholinyl | I |
| 260 | H | i-butyl | n-propyl | cyclopropyl | I |
| 261 | H | i-butyl | n-propyl | CH₂-cyclopropyl | I |
| 262 | H | i-butyl | n-propyl | 2-tetrahydrofuranyl | I |
| 263 | H | i-butyl | n-propyl | CH₂-2-tetrahydrofuran | I |
| 264 | H | i-butyl | n-propyl | 2-tetrahydrothienyl | I |
| 265 | H | cyclobutyl | n-propyl | CH₂OCH₃ | H |
| 266 | H | cyclobutyl | n-propyl | CH₃ | H |
| 267 | H | cyclobutyl | n-propyl | CH₂OH | H |
| 268 | H | cyclobutyl | n-propyl | CH₂N(CH₃)₂ | H |
| 269 | H | cyclobutyl | n-propyl | CH₂-N-piperdinyl | H |
| 270 | H | cyclobutyl | n-propyl | CH₂-N-morpholinyl | H |
| 271 | H | cyclobutyl | n-propyl | cyclopropyl | H |
| 272 | H | cyclobutyl | n-propyl | CH₂-cyclopropyl | H |
| 273 | H | cyclobutyl | n-propyl | 2-tetrahydrofuranyl | H |
| 274 | H | cyclobutyl | n-propyl | CH₂-2-tetrahydrofuran | H |
| 275 | H | cyclobutyl | n-propyl | 2-tetrahydrothienyl | H |
| 276 | H | cyclobutyl | n-propyl | CH₂OCH₃ | CF₃ |
| 277 | H | cyclobutyl | n-propyl | CH₃ | CF₃ |
| 278 | H | cyclobutyl | n-propyl | CH₂OH | CF₃ |
| 279 | H | cyclobutyl | n-propyl | CH₂N(CH₃)₂ | CF₃ |
| 280 | H | cyclobutyl | n-propyl | CH₂-N-piperdinyl | CF₃ |
| 281 | H | cyclobutyl | n-propyl | CH₂-N-morpholinyl | CF₃ |
| 282 | H | cyclobutyl | n-propyl | cyclopropyl | CF₃ |
| 283 | H | cyclobutyl | n-propyl | CH₂-cyclopropyl | CF₃ |
| 284 | H | cyclobutyl | n-propyl | 2-tetrahydrofuranyl | CF₃ |
| 285 | H | cyclobutyl | n-propyl | CH₂-2-tetrahydrofuran | CF₃ |
| 286 | H | cyclobutyl | n-propyl | 2-tetrahydrothienyl | CF₃ |
| 287 | H | cyclobutyl | n-propyl | CH₂OCH₃ | F |
| 288 | H | cyclobutyl | n-propyl | CH₃ | F |
| 289 | H | cyclobutyl | n-propyl | CH₂OH | F |
| 290 | H | cyclobutyl | n-propyl | CH₂N(CH₃)₂ | F |
| 291 | H | cyclobutyl | n-propyl | CH₂-N-piperdinyl | F |
| 292 | H | cyclobutyl | n-propyl | CH₂-N-morpholinyl | F |
| 293 | H | cyclobutyl | n-propyl | cyclopropyl | F |
| 294 | H | cyclobutyl | n-propyl | CH₂-cyclopropyl | F |
| 295 | H | cyclobutyl | n-propyl | 2-tetrahydrofuranyl | F |
| 296 | H | cyclobutyl | n-propyl | CH₂-2-tetrahydrofuran | F |
| 297 | H | cyclobutyl | n-propyl | 2-tetrahydrothienyl | F |
| 298 | H | cyclobutyl | n-propyl | CH₂OCH₃ | Cl |
| 299 | H | cyclobutyl | n-propyl | CH₃ | Cl |
| 300 | H | cyclobutyl | n-propyl | CH₂OH | Cl |
| 301 | H | cyclobutyl | n-propyl | CH₂N(CH₃)₂ | Cl |
| 302 | H | cyclobutyl | n-propyl | CH₂-N-piperdinyl | Cl |
| 303 | H | cyclobutyl | n-propyl | CH₂-N-morpholinyl | Cl |
| 304 | H | cyclobutyl | n-propyl | cyclopropyl | Cl |
| 305 | H | cyclobutyl | n-propyl | CH₂-cyclopropyl | Cl |
| 306 | H | cyclobutyl | n-propyl | 2-tetrahydrofuranyl | Cl |
| 307 | H | cyclobutyl | n-propyl | CH₂-2-tetrahydrofuran | Cl |
| 308 | H | cyclobutyl | n-propyl | 2-tetrahydrothienyl | Cl |
| 309 | H | cyclobutyl | n-propyl | CH₂OCH₃ | Br |
| 310 | H | cyclobutyl | n-propyl | CH₃ | Br |
| 311 | H | cyclobutyl | n-propyl | CH₂OH | Br |
| 312 | H | cyclobutyl | n-propyl | CH₂N(CH₃)₂ | Br |
| 313 | H | cyclobutyl | n-propyl | CH₂-N-piperdinyl | Br |
| 314 | H | cyclobutyl | n-propyl | CH₂-N-morpholinyl | Br |
| 315 | H | cyclobutyl | n-propyl | cyclopropyl | Br |
| 316 | H | cyclobutyl | n-propyl | CH₂-cyclopropyl | Br |
| 317 | H | cyclobutyl | n-propyl | 2-tetrahydrofuranyl | Br |
| 318 | H | cyclobutyl | n-propyl | CH₂-2-tetrahydrofuran | Br |
| 319 | H | cyclobutyl | n-propyl | 2-tetrahydrothienyl | Br |
| 320 | H | cyclobutyl | n-propyl | CH₂OCH₃ | I |
| 321 | H | cyclobutyl | n-propyl | CH₃ | I |
| 322 | H | cyclobutyl | n-propyl | CH₂OH | I |
| 323 | H | cyclobutyl | n-propyl | CH₂N(CH₃)₂ | I |
| 324 | H | cyclobutyl | n-propyl | CH₂-N-piperdinyl | I |
| 325 | H | cyclobutyl | n-propyl | CH₂-N-morpholinyl | I |
| 326 | H | cyclobutyl | n-propyl | cyclopropyl | I |
| 327 | H | cyclobutyl | n-propyl | CH₂-cyclopropyl | I |
| 328 | H | cyclobutyl | n-propyl | 2-tetrahydrofuranyl | I |
| 329 | H | cyclobutyl | n-propyl | CH₂-2-tetrahydrofuran | I |
| 330 | H | cyclobutyl | n-propyl | 2-tetrahydrothienyl | I |
| 331 | H | cyclopropylmethyl- | n-propyl | CH₂OCH₃ | H |
| 332 | H | cyclopropylmethyl- | n-propyl | CH₃ | H |
| 333 | H | cyclopropylmethyl- | n-propyl | CH₂OH | H |
| 334 | H | cyclopropylmethyl- | n-propyl | CH₂N(CH₃)₂ | H |
| 335 | H | cyclopropylmethyl- | n-propyl | CH₂-N-piperdinyl | H |
| 336 | H | cyclopropylmethyl- | n-propyl | CH₂-N-morpholinyl | H |
| 337 | H | cyclopropylmethyl- | n-propyl | cyclopropyl | H |
| 338 | H | cyclopropylmethyl- | n-propyl | CH₂-cyclopropyl | H |
| 339 | H | cyclopropylmethyl- | n-propyl | 2-tetrahydrofuranyl | H |
| 340 | H | cyclopropylmethyl- | n-propyl | CH₂-2-tetrahydrofuran | H |
| 341 | H | cyclopropylmethyl- | n-propyl | 2-tetrahydrothienyl | H |

-continued

| Ex.# | R | R¹ | R² | R³ | Y' |
|---|---|---|---|---|---|
| 342 | H | cyclopropylmethyl- | n-propyl | CH$_2$OCH$_3$ | CF$_3$ |
| 343 | H | cyclopropylmethyl- | n-propyl | CH$_3$ | CF$_3$ |
| 344 | H | cyclopropylmethyl- | n-propyl | CH$_2$OH | CF$_3$ |
| 345 | H | cyclopropylmethyl- | n-propyl | CH$_2$N(CH$_3$)$_2$ | CF$_3$ |
| 346 | H | cyclopropylmethyl- | n-propyl | CH$_2$-N-piperdinyl | CF$_3$ |
| 347 | H | cyclopropylmethyl- | n-propyl | CH$_2$-N-morpholinyl | CF$_3$ |
| 348 | H | cyclopropylmethyl- | n-propyl | cyclopropyl | CF$_3$ |
| 349 | H | cyclopropylmethyl- | n-propyl | CH$_2$-cyclopropyl | CF$_3$ |
| 350 | H | cyclopropylmethyl- | n-propyl | 2-tetrahydrofuranyl | CF$_3$ |
| 351 | H | cyclopropylmethyl- | n-propyl | CH$_2$-2-tetrahydrofuran | CF$_3$ |
| 352 | H | cyclopropylmethyl- | n-propyl | 2-tetrahydrothienyl | CF$_3$ |
| 353 | H | cyclopropylmethyl- | n-propyl | CH$_2$OCH$_3$ | F |
| 354 | H | cyclopropylmethyl- | n-propyl | CH$_3$ | F |
| 355 | H | cyclopropylmethyl- | n-propyl | CH$_2$OH | F |
| 356 | H | cyclopropylmethyl- | n-propyl | CH$_2$N(CH$_3$)$_2$ | F |
| 357 | H | cyclopropylmethyl- | n-propyl | CH$_2$-N-piperdinyl | F |
| 358 | H | cyclopropylmethyl- | n-propyl | CH$_2$-N-morpholinyl | F |
| 359 | H | cyclopropylmethyl- | n-propyl | cyclopropyl | F |
| 360 | H | cyclopropylmethyl- | n-propyl | CH$_2$-cyclopropyl | F |
| 361 | H | cyclopropylmethyl- | n-propyl | 2-tetrahydrofuranyl | F |
| 362 | H | cyclopropylmethyl- | n-propyl | CH$_2$-2-tetrahydrofuran | F |
| 363 | H | cyclopropylmethyl- | n-propyl | 2-tetrahydrothienyl | F |
| 364 | H | cyclopropylmethyl- | n-propyl | CH$_2$OCH$_3$ | Cl |
| 365 | H | cyclopropylmethyl- | n-propyl | CH$_3$ | Cl |
| 366 | H | cyclopropylmethyl- | n-propyl | CH$_2$OH | Cl |
| 367 | H | cyclopropylmethyl- | n-propyl | CH$_2$N(CH$_3$)$_2$ | Cl |
| 368 | H | cyclopropylmethyl- | n-propyl | CH$_2$-N-piperdinyl | Cl |
| 369 | H | cyclopropylmethyl- | n-propyl | CH$_2$-N-morpholinyl | Cl |
| 370 | H | cyclopropylmethyl- | n-propyl | cyclopropyl | Cl |
| 371 | H | cyclopropylmethyl- | n-propyl | CH$_2$-cyclopropyl | Cl |
| 372 | H | cyclopropylmethyl- | n-propyl | 2-tetrahydrofuranyl | Cl |
| 373 | H | cyclopropylmethyl- | n-propyl | CH$_2$-2-tetrahydrofuran | Cl |
| 374 | H | cyclopropylmethyl- | n-propyl | 2-tetrahydrothienyl | Cl |
| 375 | H | cyclopropylmethyl- | n-propyl | CH$_2$OCH$_3$ | Br |
| 376 | H | cyclopropylmethyl- | n-propyl | CH$_3$ | Br |
| 377 | H | cyclopropylmethyl- | n-propyl | CH$_2$OH | Br |
| 378 | H | cyclopropylmethyl- | n-propyl | CH$_2$N(CH$_3$)$_2$ | Br |
| 379 | H | cyclopropylmethyl- | n-propyl | CH$_2$-N-piperdinyl | Br |
| 380 | H | cyclopropylmethyl- | n-propyl | CH$_2$-N-morpholinyl | Br |
| 381 | H | cyclopropylmethyl- | n-propyl | cyclopropyl | Br |
| 382 | H | cyclopropylmethyl- | n-propyl | CH$_2$-cyclopropyl | Br |
| 383 | H | cyclopropylmethyl- | n-propyl | 2-tetrahydrofuranyl | Br |
| 384 | H | cyclopropylmethyl- | n-propyl | CH$_2$-2-tetrahydrofuran | Br |
| 385 | H | cyclopropylmethyl- | n-propyl | 2-tetrahydrothienyl | Br |
| 386 | H | cyclopropylmethyl- | n-propyl | CH$_2$OCH$_3$ | I |
| 387 | H | cyclopropylmethyl- | n-propyl | CH$_3$ | I |
| 388 | H | cyclopropylmethyl- | n-propyl | CH$_2$OH | I |
| 389 | H | cyclopropylmethyl- | n-propyl | CH$_2$N(CH$_3$)$_2$ | I |
| 390 | H | cyclopropylmethyl- | n-propyl | CH$_2$-N-piperdinyl | I |
| 391 | H | cyclopropylmethyl- | n-propyl | CH$_2$-N-morpholinyl | I |
| 392 | H | cyclopropylmethyl- | n-propyl | cyclopropyl | I |
| 393 | H | cyclopropylmethyl- | n-propyl | CH$_2$-cyclopropyl | I |
| 394 | H | cyclopropylmethyl- | n-propyl | 2-tetrahydrofuranyl | I |
| 395 | H | cyclopropylmethyl- | n-propyl | CH$_2$-2-tetrahydrofuran | I |
| 396 | H | cyclopropylmethyl- | n-propyl | 2-tetrahydrothienyl | I | or a pharmaceutically acceptable salt thereof.

\* \* \* \* \*